US008202968B2

(12) United States Patent
You et al.

(10) Patent No.: US 8,202,968 B2
(45) Date of Patent: Jun. 19, 2012

(54) PREDICTING LUNG CANCER SURVIVAL USING GENE EXPRESSION

(75) Inventors: Ming You, St. Louis, MO (US); Yan Lu, St. Louis, MO (US); Ramaswamy Govindan, St. Louis, MO (US); Mark A. Watson, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 12/445,596

(22) PCT Filed: Oct. 19, 2007

(86) PCT No.: PCT/US2007/081938
§ 371 (c)(1),
(2), (4) Date: May 18, 2010

(87) PCT Pub. No.: WO2008/070301
PCT Pub. Date: Jun. 12, 2008

(65) Prior Publication Data
US 2010/0267574 A1    Oct. 21, 2010

Related U.S. Application Data

(60) Provisional application No. 60/862,290, filed on Oct. 20, 2006.

(51) Int. Cl.
*C07K 14/00* (2006.01)
*C07H 21/04* (2006.01)
(52) U.S. Cl. ....................... 530/350; 536/23.5
(58) Field of Classification Search .................. None
See application file for complete search history.

(56) References Cited

FOREIGN PATENT DOCUMENTS
WO     02/44331       6/2002
WO     WO 02/44331  *  6/2002

OTHER PUBLICATIONS

Bremnes et al (J Clinical Oncology, 2002, 20:2417-2428).*
Lu et al (PLOS Medicine, 2006, 3:2229-2242, IDS).*
Yoo et al (APMIS, 2002, 110:825-832).*
Bach, P., et al., "Screening for lung cancer: a review of the current literature," Chest, Jan. 2003, pp. 72S-82S, vol. 123 (1 Suppl.).
Baldus, S., et al., "MUCI and nuclear beta-catenin are coexpressed at the invasion front of colorectal carcinomas and are both correlated with tumor prognosis," Clin. Cancer Res., Apr. 15, 2004, pp. 2790-2796, vol. 10, No. 8.
Benito, M., et al., "Adjustment of systematic microarray data biases," Bioinformatics, Jan. 1, 2004, pp. 105-114, vol. 20, No. 1.
Bhattacharjee, A., et al., "Classification of human lung carcinomas by mRNA expression profiling reveals distinct adenocarcinoma subclasses," Proc. Natl. Acad. Sci., Nov. 20, 2001, pp. 13790-13795, vol. 98, No. 24.

Borczuk, A., et al., "Molecular signatures in biopsy specimens of lung cancer," Am. J. Respir. Crit. Care Med., Jul. 15, 2004, pp. 167-174, vol. 170, No. 2.
Brabender, J., et al., "Adenomatous polyposis coli gene promoter hypermethylation in non-small cell lung cancer is associated with survival," Oncogene, Jun. 14, 2001, pp. 3528-3532, vol. 20, No. 27.
Chaparro, J., et al., "Alterations in thigh subcutaneous adipose tissue gene expression in protease inhibitor-based highly active antiretroviral therapy," Metabolism, May 2005, pp. 561-567, vol. 54, No. 5.
Chen, X., et al., "Variation in gene expression patterns in human gastric cancers," Mol. Biol. Cell, Aug. 2003, pp. 3208-3215, vol. 14, No. 8.
Chung, C., et al., "Molecular classification of head and neck squamous cell carcinomas using patterns of gene expression," Cancer Cell, May 2004, pp. 489-500, vol. 5, No. 5.
Doubre, H., et al., "Multidrop resistance-associated protein (MRP1) is overexpressed in DNA aneuploid carcinomatous cells in non-small cell lung cancer (NSCLC)," Int. J. Cancer, Feb. 10, 2005, pp. 568-574, vol. 113, No. 4.
Eberhart, C., et al., "Histopathological and molecular prognostic markers in medulloblastoma: c-myc, N-myc, TrkC, and anaplasia," J. Neuropathol. Exp. Neurol., May 2004, pp. 441-449, vol. 63, No. 5.
Freije, W., et al., "Gene expression profiling of gliomas strongly predicts survival," Cancer Res., Sep. 15, 2004, pp. 6503-6510, vol. 64, No. 18.
Garber M., et al., "Diversity of gene expression in adenocarcinoma of the lung," Proc. Natl. Acad. Sci. USA, Nov. 20, 2001, pp. 13784-13789, vol. 98, No. 24.
Hu, Z., et al., "The molecular portraits of breast tumors are conserved across microarray platforms," BMC Genomics, Apr. 27, 2006, vol. 7, No. 96, 12 pages.
Irizarry, R., et al., "Summaries of Affymetrix GeneChip probe level data," Nucleic Acids Res., Feb. 15, 2003, p. e15, vol. 31, No. 4.
Jung, S., et al., "Immunoreactivty of CD10 and inhibin alpha in differentiating hemangioblastoma of central nervous system from metastatic clear cell renal cell carcinoma," Mod. Pathol., 2005, pp. 788-794, vol. 18.
Li, H., et al., "Partial Cox regression analysis for high-dimensional microarray gene expression," Bioinformatics, Aug. 4, 2004, pp. i208-i215, vol. 20 Supp. 1.
Liu, G., et al., "NetAffx: Affymetrix probe sets and annotations," Nucl. Acids Res., Jan. 1, 2003, pp. 82-86, vol. 31, No. 1.
Lu et al., "A gene expression signature predicts survival of patients with stage I non-small cell lung cancer," PLOS Medicine, Dec. 2006, pp. 2229-2243, vol. 3, No. 12.
Macheda, M., et al., "Molecular and cellular regulation of glucose transporter (GLUT) proteins in cancer," J. Cell Physiol., Mar. 2005, pp. 654-662, vol. 202, No. 3.

(Continued)

*Primary Examiner* — Laura B Goddard
(74) *Attorney, Agent, or Firm* — Polsinelli Shughart PC

(57) ABSTRACT

The present invention provides a plurality of biomarkers for predicting survival of a subject with a lung cancer. More specifically, the present invention relates to methods of predicting survival of a subject with a lung cancer, a kit for predicting survival of a subject with a lung cancer, and an array for predicting survival of a subject with lung cancer.

1 Claim, 8 Drawing Sheets

OTHER PUBLICATIONS

Martin, B., et al., "Role of Bcl-2 as a prognostic factor for survival in lung cancer: a systematic review of the literature with meta-analysis," Br. J. Cancer, Jul. 7, 2003, pp. 55-64, vol. 89, No. 1.

Mountain, C., et al., "Regional lymph node classification for lung cancer staging," Chest, Jun. 1997, pp. 1718-1723, vol. 111, No. 6.

Oh, D., et al., "Estrogen-regulated genes predict survival in hormone receptor-positive breast cancers," J. Clin. Oncol., Apr. 10, 2006, pp. 1656-1664, vol. 24, No. 11.

Perreard, L., et al., "Classification and risk stratification of invasive breast carcinomas using a realtime quantitative RT-PCR assay," Breast Cancer Res., Apr. 20, 2006, p. R23, vol. 8, No. 2.

Rosenwald, A., "The use of molecular profiling to predict survival after chemotherapy for diffuse large-B-cell lymphoma," Jun. 20, 2002, N. Engl. J. Med., pp. 1937-1947, vol. 346, No. 25.

Schaich, M., et al., "MDR1 and MRP1 gene expression are independent predictors for treatment outcome in adult acute myeloid leukemia," Br. J. Haematol., Feb. 2005, pp. 324-332, vol. 128, No. 3.

Shai, R., et al., "Gene expression profiling identifies molecular subtypes of gliomas," Oncogene, Jul. 31, 2003, pp. 4918-4923, vol. 22, No. 31.

Shivapurkar, N., et al., Loss of expression of death-inducing signaling complex (DISC) components in lung cancer cell lines and the influence of MYC amplification, Oncogene, Dec. 5, 2002, pp. 8510-8514, vol. 21, No. 55.

Sorlie, T., "Gene expression patterns of breast carcinomas distinguish tumor subclasses with clinical implications," Proc. Natl. Acad. Sci. USA, Sep. 11, 2001, pp. 10869-10874, vol. 98, No. 19.

Sotiriou, C., et al., "Breast cancer classification and prognosis based on gene expression profiles from a population based study," Proc. Natl. Acad. Sci. USA, Sep. 2, 2003, pp. 10393-10398, vol. 100, No. 18.

Spiro, S., et al., "One hundred years of lung cancer," Am. J. Respir. Crit. Care Med., Sep. 1, 2005, pp. 523-529, vol. 172, No. 5.

Sun, Z., et al., "Can gene expression profiling predict survival for patients with squamous cell carcinoma of the lung?" Mol. Cancer, Dec. 3, 2004, p. 35, vol. 3, No. 1.

Van De Vijver, J., et al., "A gene expression signature as a predictor of survival in breast cancer," N. Engl. J. Med., Dec. 19, 2002, pp. 1999-2009, vol. 347, No. 25.

Vasselli, J., et al., "Predicting survival in patients with metastatic kidney cancer by gene-expression profiling in the primary tumor," Proc. Natl. Acad. Sci. USA, Jun. 10, 2003, pp. 6958-6963, vol. 100, No. 12.

Wigle, D., et al., "Molecular profiling of non-small cell lung cancer and correlation with disease-free survival," Cancer Res., Jun. 1, 2002, pp. 3005-3008, vol. 62, No. 11.

Xu, L., et al., "Robust prostate cancer marker genes emerge from direct integration of inter-study microarray data," Bioinformatics, Oct. 15, 2005, pp. 3905-3911, vol. 21, No. 20.

Yamagata, N., et al., "A training-testing approach to the molecular classification of resected non-small cell lung cancer," Clin. Cancer Res., Oct. 15, 2003, pp. 4695-4704, vol. 9, No. 13.

Yilmaz, A., et al., "Distribution of Bcl-2 gene expression and its prognostic value in non-small cell lung cancer," Tuberk Toraks, 2005, pp. 323-329, vol. 53, No. 4.

Younes, M., et al., "Overexpression of Glut1 and Glut3 in stage I nonsmall cell lung carcinoma is associated with poor survival," Cancer, Sep. 15, 1997, pp. 1046-1051, vol. 80, No. 6.

Baltagi, B., "Econometric Analysis of Panel Data", John Wiley and Sons, Ltd. 2001.

Beer, D., et al., "Geneexpression profiles predict survival of patients with lung adenocarcinoma," Nature Med., Aug. 2002, pp. 816-824, vol. 8, No. 8.

Bild, A. et al., "Oncogenic pathway signatures in human cancers as a guide to targeted therapies," Nature, Jan. 19, 2006, pp. 353-357, vol. 439, No. 7074.

Chen, H., "Aberrant methylation of FBN2 in human non-small cell lung cancer," Lung Cancer, Oct. 2005, pp. 43-49, vol. 50, No. 1.

Drexler, H., et al., "FLT3: receptor and ligand," Growth Factors, Jun. 2004, pp. 71-73, vol. 22, No. 2.

El-Sherif, A., et al., "New therapeutic approaches for early stage non-small cell lung cancer," Sug. Oncol., Jul. 2005, pp. 27-32, vol. 14., No. 1.

Yang, P., et al., "Role of the Glutathione Metabolic Pathway in Lung Cancer Treatment and Prognosis: A Review," J. Clin. Oncol., Apr. 10, 2006, pp. 1761-1769, vol. 24, No. 11.

Guo, W., et al., "Identification of Differentially Expressed Genes Contributing to Radioresistance in Lung Cancer Cells using Microarray Analysis," Radiat. Res., Jul. 2005, pp. 27-35, vol. 164, No. 1.

Ihaka, R., et al., "A language for data analysis and graphics," J. Comput Graph. Statist. 1996, pp. 299-314, vol. 5.

Livak, K., et al, "Analysis of relative gene expression data using realtime quantitative PCR and the 2(-Delta Delta CT (T)) Methods," Methods, Dec. 2001, pp. 402-408, vol. 25, No. 4.

Mattern, J., et al., "Characteristics of long-term survivors of untreated lung cancer," Lung Cancer, Jun. 2002, pp. 277-282, vol. 36, No. 3.

Minami, K., et al., "Prognostic significance of p53, K-67, VEGF and Glut-1 in resected stage I adenocarcinoma of the lung," Lung Cancer, Oct. 2002, pp. 51-57, vol. 38, No. 1.

Pomeroy, SL., et al., "Prediction of central nervous system embryonal tumour outcome based on gene expression," Nature, Jan. 24, 2002, pp. 436-442, Vol. 415, No. 6870.

Roukos, D., et al., "Perspectives in the treatment of gastric cancer," Nat. Clin. Pract. Oncol., Feb. 2005, pp. 98-107, vol. 2, No. 2.

Van'T Veer, L, et al., "Gene expression profiling predicts clinical outcome of breast cancer," Nature 2002, pp. 530-536, vol. 415.

Wang, Y., et al., "Gene-expression profiles to predict distant metastasis of lymph-node-negative primary breast cancer," Feb. 19-25, 2005, pp. 671-679, vol. 365, No. 9460.

* cited by examiner

US 8,202,968 B2

PREDICTING LUNG CANCER SURVIVAL USING GENE EXPRESSION

GOVERNMENTAL RIGHTS

The present invention was made, at least in part, with support by the National Institutes of Health grant numbers CA099187, CA099147, ES012063, and ES013340. Accordingly, the United States Government may have certain rights in the invention.

FIELD OF THE INVENTION

The present invention generally relates to a plurality of biomarkers for predicting survival. More specifically, the present invention relates to methods of predicting survival of a subject with cancer.

BACKGROUND OF THE INVENTION

Lung cancer is the leading cause of cancer death in men and women in the United States. Non-small cell lung cancer (NSCLC) accounts for more than 87% of all lung cancers diagnosed in the U.S. Despite major advances in recent years, most lung cancers have disseminated at the time of presentation and affected individuals have a mortality rate of nearly 90%.

This high mortality is mainly due to the absence of an effective screening strategy to identify lung cancer at an early curable stage. Thus, only ~25% of patients presenting with lung cancer are in a sufficiently early stage to be amenable to effective surgical treatment. The patients with stage I or II NSCLC have an ~50% five year survival rate after surgery alone, compared to less than 5% five-year survival rate for patients with advanced lung cancer (stages IIIb and IV).

Patients diagnosed with stage I NSCLC usually undergo surgical resection. Yet, nearly 50% of patients with stage I or II NSCLC will die from recurrent disease despite surgical resection. There are no reliable clinical or molecular predictors for identifying those at high risk for developing recurrent therapy.

There is, therefore, a critical need in the art to identify a reliable molecular signature in the tumor that could identify those who are likely to develop recurrent disease. If such biomarkers are identified, adjuvant therapy could be selectively administered to those at high risk for relapse. Conversely, the low risk group can be spared the side effects of adjuvant therapy.

SUMMARY OF THE INVENTION

Among the several aspects of the invention is provided a method for predicting survival of a subject with lung cancer. The method comprises measuring the expression of a plurality of biomarkers in a sample of cells from the subject. The expression value of each biomarker is determined, and the expression values are analyzed to generate a risk score of survival. A risk score with a positive value is indicative of a short survival time and a risk score with a negative value is indicative of a long survival time.

An additional aspect is a plurality of biomarkers for predicting survival of a subject with a lung cancer. The biomarkers comprise APC, ARHGEF1, BCL2, CASP10, CASP8, CCR2, CDH8, DTNA, ENPP2, FUCA1, GNAT2, GOLGA1, IL8RB, ITSN1, MAP4K1, MEF2C, MLLT10, NR1H4, NTRK3, PBP, PIGC, PIK3R1, PKNOX1, PPDX, PRKACA, RAB28, RAE1, SNX1, SON, TMSB4X, TRA2A, ZNFN1A1, ABCC1, ADAM17, ARL4A, BIK, BLM, CHERP, CRABP1, DSP, FBN2, GLI2, HNRPD, INHA, IRS1, LARS2, LY6D, NID, NOTCH3, PCDHGA12, PFN2, PLEC1, PSEN1, PYGL, SLC2A1, SLC7A1, SMC1L1, SMARCA3, STC1, UPK2, VGLL1, ZNF154, ZNF410, and ZWINTAS.

In yet another aspect, the invention provides a kit for predicting survival of a subject with a lung cancer. The kit comprises a plurality of agents for measuring the expression of a plurality of biomarkers, means for converting the expression of each biomarker into an expression value, and means for analyzing the expression values to generate a risk score that predicts survival time.

In still another aspect, the invention provides an array comprising nucleic acids capable of hybridizing to the mRNAs of the following biomarkers: APC, ARHGEF1, BCL2, CASP10, CASP8, CCR2, CDH8, DTNA, ENPP2, FUCA1, GNAT2, GOLGA1, IL8RB, ITSN1, MAP4K1, MEF2C, MLLT10, NR1H4, NTRK3, PBP, PIGC, PIK3R1, PKNOX1, PPDX, PRKACA, RAB28, RAE1, SNX1, SON, TMSB4X, TRA2A, ZNFN1A1, ABCC1, ADAM17, ARL4A, BIK, BLM, CHERP, CRABP1, DSP, FBN2, GLI2, HNRPD, INHA, IRS1, LARS2, LY6D, NID, NOTCH3, PCDHGA12, PFN2, PLEC1, PSEN1, PYGL, SLC2A1, SLC7A1, SMC1L1, SMARCA3, STC1, UPK2, VGLL1, ZNF154, ZNF410, and ZWINTAS.

Other aspects and iterations of the invention are described more thoroughly below.

DETAILED DESCRIPTION OF THE INVENTION

Figure 1:
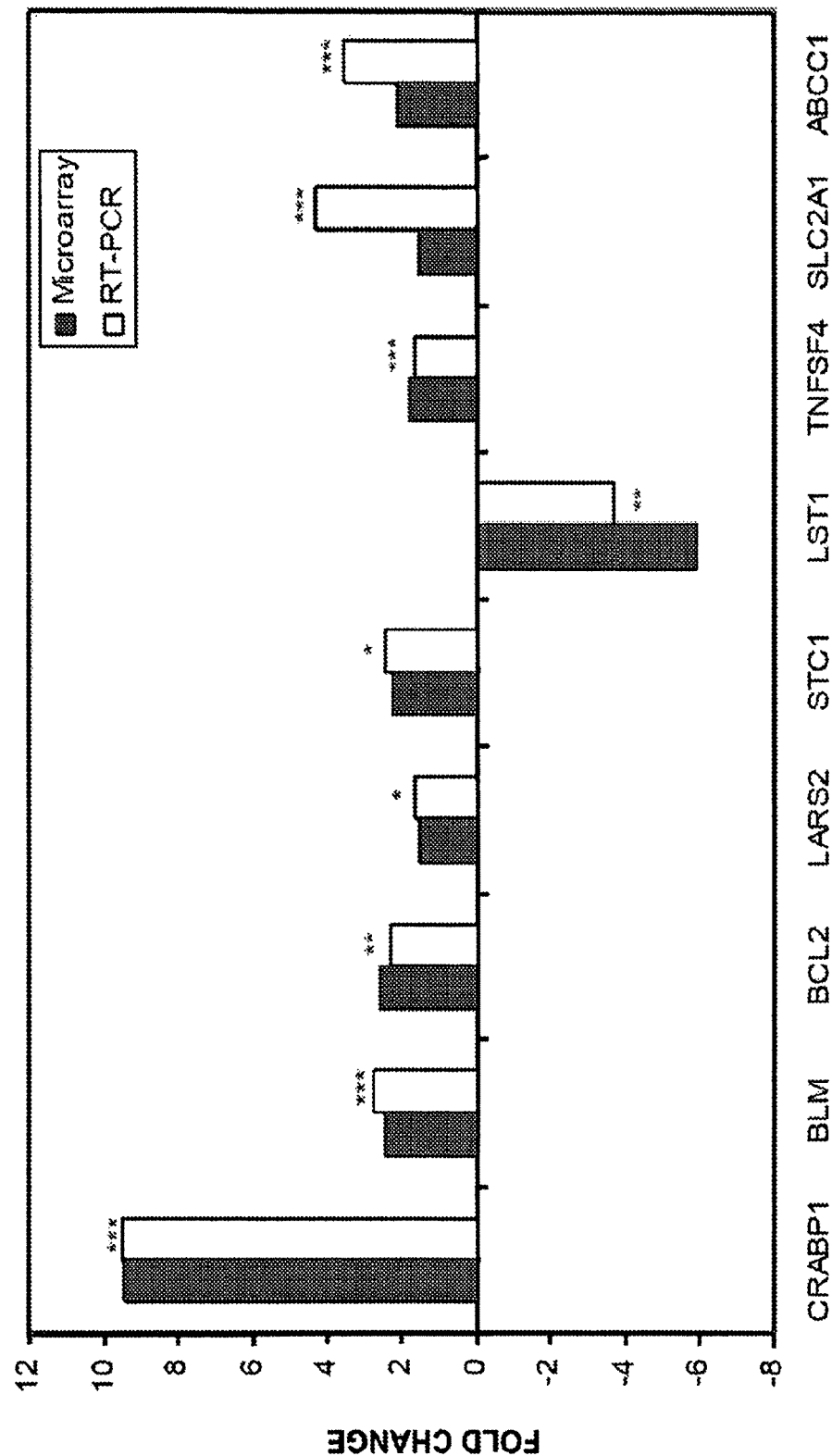
FIG. 1 is a graph depicting real time PCR validation of several candidate survival-related genes identified by gene expression profiling. Bars represent fold changes for the selected genes with differential expression between long-term survival (>5 years) and short-term survival (<2 years) patients. Positive fold change represents up regulation and negative fold change represent down regulation in short-term survival patients. *: $p \leq 0.05$; : $p \leq 0.01$; *: $p \leq 0.005$.

The present invention provides methods for predicting survival of a subject with cancer. The prediction method is based upon the differential expression of a plurality of biomarkers in cancer cells. It was discovered that some biomarkers tend to be over-expressed in short-term cancer survivors, whereas other biomarkers tend to be over-expressed in long-term cancer survivors. The unique pattern of expression of these biomarkers in a sample of cells from a subject with cancer may be used to predict relative survival time, and ultimately the prognosis, for that subject.

(I) Method for Predicting Survival of a Subject with Cancer

One aspect of the invention provides a method for predicting cancer survival. The method comprises determining the differential expression of a plurality of biomarkers in a sample of cells from a subject with cancer. The biomarker expression signature of the cancer may be used to derive a risk score that is predictive of survival from that cancer. The score may indicate low risk, such that the subject may survive a long time (i.e., longer than 5 years), or the score may indicate high risk, such that the subject may not survive a long time (i.e., less than two years).

(a) Survival-Related Biomarkers

A meta-analysis of data sets from five different microarray studies on lung cancer revealed 64 biomarkers whose expression is highly related to cancer survival (see Table A). Some of the biomarkers are over-expressed in long-term survivors (Table B), and some of the biomarkers are over-expressed in short-term survivors (Table C). A biomarker may play a role in cancer metastasis by affecting cell adhesion (e.g., APC, CDH8, DSP, LY6D, PCDHGA12, and NID), cell motility (e.g., IL8RB, ENPP2, and CCR2), or inflammation and immune responses (e.g., CASP8 and CASP10). A biomarker may also be involved in apoptosis (e.g., INHA, PSEN1, CASP8, CASP10, PIK3R1, BCL2, and BIK). A biomarker may play a role in transport mechanisms (e.g., ABCC1, ITSN1, CRABP1, SLC2A1, and ZWINTAS). A biomarker may also be associated with survival in other types of cancer including breast cancer, brain cancer, and gastric cancer (e.g., ABCC1, APC, ARHGEF1, BCL2, BLM, CASP10, CDH8, CHERP, CRABP1, DSP, ENPP2, FBN2, FUCA1, GLI2, HNRPD, IL8RB, INHA, IRS1, ITSN1, LY6D, PIK3R1, PLEC1, PBP, PRKACA, PYGL, SLC2A1, SLC7A1, SMC1L1, STC1, TMSB4X, VGLL1, and ZWINTAS).

TABLE A

Survival-related Biomarkers

| Official Name | Gene Annotation | Accession No. |
|---|---|---|
| ABCC1 | ATP-binding cassette sub-family C (CFTR/MRP) member 1 | AF022853, X78338, L05628, AI539710 |
| ADAM17 | ADAM metallopeptidase domain 17 (tumor necrosis factor alpha converting enzyme) | AA142964, U69611, U86755, AI797833 |
| APC | Adenomatosis polyposis coli | AF038181, M73548 |
| ARHGEF1 | Rho guanine nucleotide exchange factor (GEF) 1 | Y09160, U64105, NM_004706 |
| ARL4A | ADP-ribosylation factor-like 4A | U73960, NM_005738 |
| BCL2 | B-cell CLL/lymphoma 2 | M13994, M13995, M14745, NM_000657 |
| BIK | BCL2-interacting killer (apoptosis-inducing) | U34584, X89986, NM_001197 |
| BLM | Bloom syndrome | U39817, NM_000057 |
| CASP10 | caspase 10 apoptosis-related cysteine peptidase | U86214, U60519, AF111344 |
| CASP8 | caspase 8 apoptosis-related cysteine peptidase | X98172, BF439983 |
| CCR2 | chemokine (C-C motif) receptor 2 | NM_000647 |
| CDH8 | cadherin 8 type 2 | L34060, AB035305 |
| CHERP | calcium homeostasis endoplasmic reticulum protein | Y08265, NM_006387 |
| CRABP1 | cellular retinoic acid binding protein 1 | S74445, NM_004378 |
| DSP | desmoplakin | AL031058, NM_004415 |
| DTNA | dystrobrevin alpha | U46746, U84540, U84551, NM_001390 |
| ENPP2 | ectonucleotide pyrophosphatase/phosphodiesterase 2 (autotaxin) | L35594, D45421 |
| FBN2 | fibrillin 2 (congenital contractural arachnodactyly) | U03272, NM_001999 |
| FUCA1 | fucosidase alpha-L-1 tissue | M29877, NM_000147 |
| GLI2 | GLI-Kruppel family member GLI2 | AB007296, D14827, NM_030379 |
| GNAT2 | guanine nucleotide binding protein (G protein) alpha transducing activity polypeptide 2 | D10384, Z18859, BC000233 |
| GOLGA1 | golgi autoantigen golgin subfamily a, 1 | AL050012, U51587, AW675473 |
| HNRPD | heterogeneous nuclear ribonucleoprotein D (AU-rich element RNA binding protein 1, 37 kDa) | M94630, HG2538-HT2634, D55672 |
| IL8RB | interleukin 8 receptor beta | L19593, U11872, NM_001557 |
| INHA | inhibin alpha | M13981 |
| IRS1 | insulin receptor substrate 1 | S62539, S85963, NM_005544 |
| ITSN1 | intersectin 1 (SH3 domain protein) | AF003738, U61166 |
| LARS2 | leucyl-tRNA synthetase 2 mitochondrial | D21851, NM_015340 |
| LY6D | lymphocyte antigen 6 complex locus D | Y12642, X82693, NM_003695 |
| MAP4K1 | mitogen-activated protein kinase kinase kinase kinase 1 | U66464, BE646618 |
| MEF2C | MADS box transcription enhancer factor 2 polypeptide C (myocyte enhancer factor 2C) | S57212, L08895, NM_002397 |
| MLLT10 | myeloid/lymphoid or mixed-lineage leukemia (trithorax homolog Drosophila); translocated to, 10 | U13948, NM_004641 |
| NID | nidogen 1 NID1 | M30269, BF940043 |
| NOTCH3 | Notch homolog 3 (Drosophila) | U97669, X79439, NM_000435 |
| NR1H4 | nuclear receptor subfamily 1 group H member 4 | U68233, NM_005123 |
| NTRK3 | neurotrophic tyrosine kinase, receptor, type 3 | U05012, S76475, AF041811 |
| PBP | phosphatidylethanolamine binding protein 1 PEBP1 | X75252, NM_002567, AF130103 |
| PCDHGA12 | protocadherin gamma subfamily A, 12 | AB000897 |
| PFN2 | profilin 2 | L10678, NM_002628 |
| PIGC | phosphatidylinositol glycan class C | AL035301, D85418 |
| PIK3R1 | phosphoinositide-3-kinase regulatory subunit 1 (p85 alpha) | M61906, AI679268 |
| PKNOX1 | PBX/knotted 1 homeobox 1 | U68727, NM_004571 |
| PLEC1 | plectin 1 intermediate filament binding protein 500 kDa | HG3132, HT3308, Z54367 |
| PPOX | protoporphyrinogen oxidase | D38537, NM_000309 |
| PRKACA | protein kinase cAMP-dependent catalytic, alpha | M80335, X07767 |
| PSEN1 | presenilin 1 (Alzheimer disease 3) | L76517, L76528, NM_007318 |

TABLE A-continued

Survival-related Biomarkers

| Official Name | Gene Annotation | Accession No. |
|---|---|---|
| PYGL | phosphorylase glycogen; liver (Hers disease glycogen storage disease type VI) | AF046798, M14636, NM_002863 |
| RAB28 | RAB28 member RAS oncogene family | X94703, NM_004249 |
| RAE1 | RAE1 RNA export 1 homolog (S. pombe) | U84720, U85943 |
| SLC2A1 | solute carrier family 2 (facilitated glucose transporter) member 1 | K03195, AI091047 |
| SLC7A1 | solute carrier family 7 (cationic amino acid transporter y+ system) | AL050021, X57303, AA148507 |
| SMARCA3 | SWI/SNF related matrix associated actin dependent regulator of chromatin, subfamily a, member 3 | Z46606, L34673, AI760760 |
| SMC1L1 | SMC1 structural maintenance of chromosomes 1-like 1 (yeast) | D80000, S78271 |
| SNX1 | sorting nexin 1 | AL050148, U53225, AI052536 |
| SON | SON DNA binding protein | AB028942, X63753, AI936458 |
| STC1 | stanniocalcin 1 | U25997, NM_003155 |
| TMSB4X | thymosin beta 4, X-linked | M17733, AL133228 |
| TRA2A | transformer-2 alpha | AW026656, U53209, AA831170 |
| UPK2 | uroplakin 2 | Y13645, AF000562, NM_006760 |
| VGLL1 | vestigial like 1 (Drosophila) | Z97632, AC000115, NM_016267, BE542323 |
| ZNF154 | zinc finger protein 154 (pHZ-92) | U20648 |
| ZNF410 | zinc finger protein 410 | U90919, NM_021188 |
| ZNFN1A1 | zinc finger protein subfamily 1A, 1 | U40462, NM_006060 |
| ZWINTAS | ZW10 interactor antisense | X98261 |

TABLE B

Biomarkers over-expressed in long-term survivors

APC, ARHGEF1, BCL2, CASP10, CASP8, CCR2, CDH8, DTNA, ENPP2, FUCA1, GNAT2, GOLGA1, IL8RB, ITSN1, MAP4K1, MEF2C, MLLT10, NR1H4, NTRK3, PBP, PIGC, PIK3R1, PKNOX1, PPOX, PRKACA, RAB28, RAE1, SNX1, SON, TMSB4X, TRA2A, ZNFN1A1

TABLE C

Biomarkers over-expressed in short-term survivors

ABCC1, ADAM17, ARL4A, BIK, BLM, CHERP, CRABP1, DSP, FBN2, GLI2, HNRPD, INHA, IRS1, LARS2, LY6D, NID, NOTCH3, PCDHGA12, PFN2, PLEC1, PSEN1, PYGL, SLC2A1, SLC7A1, SMARCA3, SMC1L1, STC1, UPK2, VGLL1, ZNF410, ZNF154, ZWINTAS (b) Measuring Expression of a Plurality of Biomarkers The method entails measuring the differential expression of a plurality of survival-related biomarkers in a sample of cells from a subject with cancer. The differential pattern of expression in each cancer—or gene expression signature—may then be used to generate a risk score that is predictive of cancer survival. The level of expression of a biomarker may be increased or decreased in a subject relative to other subjects with cancer. The expression of a biomarker may be higher in long-term survivors than in short-term survivors. Alternatively, the expression of a biomarker may be higher in short-term survivors than in long-term survivors.

The differential expression of a plurality of biomarkers may be measured by a variety of techniques that are well known in the art. Quantifying the levels of the messenger RNA (mRNA) of a biomarker may be used to measure the expression of the biomarker. Alternatively, quantifying the levels of the protein product of a biomarker may be to measure the expression of the biomarker. Additional information regarding the methods discussed below may be found in Ausubel et al., (2003) Current Protocols in Molecular Biology, John Wiley & Sons, New York, N.Y., or Sambrook et al. (1989) Molecular Cloning: A Laboratory Manual, Cold Spring Harbor Press, Cold Spring Harbor, N.Y. One skilled in the art will know which parameters may be manipulated to optimize detection of the mRNA or protein of interest.

A nucleic acid microarray may be used to quantify the differential expression of a plurality of biomarkers. Microarray analysis may be performed using commercially available equipment, following manufacturer's protocols, such as by using the Affymetrix GeneChip® technology (Santa Clara, Calif.) or the Microarray System from Incyte (Fremont, Calif.). Typically, single-stranded nucleic acids (e.g., cDNAs or oligonucleotides) are plated, or arrayed, on a microchip substrate. The arrayed sequences are then hybridized with specific nucleic acid probes from the cells of interest. Fluorescently labeled cDNA probes may be generated through incorporation of fluorescently labeled deoxynucleotides by reverse transcription of RNA extracted from the cells of interest. Alternatively, the RNA may be amplified by in vitro transcription and labeled with a marker, such as biotin. The labeled probes are then hybridized to the immobilized nucleic acids on the microchip under highly stringent conditions. After stringent washing to remove the non-specifically bound probes, the chip is scanned by confocal laser microscopy or by another detection method, such as a CCD camera. The raw fluorescence intensity data in the hybridization files are generally preprocessed with the robust multichip average (RMA) algorithm to generate expression values.

Quantitative real-time PCR (QRT-PCR) may also be used to measure the differential expression of a plurality of biomarkers. In QRT-PCR, the RNA template is generally reverse transcribed into cDNA, which is then amplified via a PCR reaction. The amount of PCR product is followed cycle-by-cycle in real time, which allows for determination of the initial concentrations of mRNA. To measure the amount of PCR product, the reaction may be performed in the presence of a fluorescent dye, such as SYBR Green, which binds to double-stranded DNA. The reaction may also be performed with a fluorescent reporter probe that is specific for the DNA being amplified. A non-limiting example of a fluorescent reporter probe is a TaqMan® probe (Applied Biosystems, Foster City, Calif.). The fluorescent reporter probe fluoresces when the quencher is removed during the PCR extension cycle. Muliplex QRT-PCR may be performed by using multiple gene-specific reporter probes, each of which contains a different fluorophore. Fluorescence values are recorded during each cycle and represent the amount of product amplified to that point in the amplification reaction. To minimize errors and reduce any sample-to-sample variation, QRT-PCR is typically performed using a reference standard. The ideal reference standard is expressed at a constant level among different tissues, and is unaffected by the experimental treatment. Suitable reference standards include, but are not limited to, mRNAs for the housekeeping genes glyceraldehyde-3-phosphate-dehydrogenase (GAPDH) and beta-actin. The level of mRNA in the original sample or the fold change in expression of each biomarker may be determined using calculations well known in the art.

Immunohistochemical staining may also be used to measure the differential expression of a plurality of biomarkers.

This method enables the localization of a protein in the cells of a tissue section by interaction of the protein with a specific antibody. For this, the tissue may be fixed in formaldehyde or another suitable fixative, embedded in wax or plastic, and cut into thin sections (from about 0.1 mm to several mm thick) using a microtome. Alternatively, the tissue may be frozen and cut into thin sections using a cryostat. The sections of tissue may be arrayed onto and affixed to a solid surface (i.e., a tissue microarray). The sections of tissue are incubated with a primary antibody against the antigen of interest, followed by washes to remove the unbound antibodies. The primary antibody may be coupled to a detection system, or the primary antibody may be detected with a secondary antibody that is coupled to a detection system. The detection system may be a fluorophore or it may be an enzyme, such as horseradish peroxidase or alkaline phosphatase, which can convert a substrate into a colorimetric, fluorescent, or chemiluminescent product. The stained tissue sections are generally scanned under a microscope. Because a sample of tissue from a subject with cancer may be heterogeneous, i.e., some cells may be normal and other cells may be cancerous, the percentage of positively stained cells in the tissue may be determined. This measurement, along with a quantification of the intensity of staining, may be used to generate an expression value for the biomarker.

An enzyme-linked immunosorbent assay, or ELISA, may be used to measure the differential expression of a plurality of biomarkers. There are many variations of an ELISA assay. All are based on the immobilization of an antigen or antibody on a solid surface, generally a microtiter plate. The original ELISA method comprises preparing a sample containing the biomarker proteins of interest, coating the wells of a microtiter plate with the sample, incubating each well with a primary antibody that recognizes a specific antigen, washing away the unbound antibody, and then detecting the antibody-antigen complexes. The antibody-antibody complexes may be detected directly. For this, the primary antibodies are conjugated to a detection system, such as an enzyme that produces a detectable product. The antibody-antibody complexes may be detected indirectly. For this, the primary antibody is detected by a secondary antibody that is conjugated to a detection system, as described above. The microtiter plate is then scanned and the raw intensity data may be converted into expression values using means known in the art.

An antibody microarry may also be used to measure the differential expression of a plurality of biomarkers. For this, a plurality of antibodies is arrayed and covalently attached to the surface of the microarray or biochip. A protein extract containing the biomarker proteins of interest is generally labeled with a fluorescent dye. The labeled biomarker proteins are incubated with the antibody microarry. After washes to remove the unbound proteins, the microarray is scanned. The raw fluorescent intensity data maybe converted into expression values using means known in the art.

Luminex multiplexing microspheres may also be used to measure the differential expression of a plurality of biomarkers. These microscopic polystyrene beads are internally color-coded with fluorescent dyes, such that each bead has a unique spectral signature (of which there are up to 100). Beads with the same signature are tagged with a specific oligonucleotide or specific antibody that will bind the target of interest (i.e., biomarker mRNA or protein, respectively). The target, in turn, is also tagged with a fluorescent reporter. Hence, there are two sources of color, one from the bead and the other from the reporter molecule on the target. The beads are then incubated with the sample containing the targets, of which up 100 may be detected in one well. The small size/surface area of the beads and the three dimensional exposure of the beads to the targets allows for nearly solution-phase kinetics during the binding reaction. The captured targets are detected by high-tech fluidics based upon flow cytometry in which lasers excite the internal dyes that identify each bead and also any reporter dye captured during the assay. The data from the acquisition files may be converted into expression values using means known in the art.

In situ hybridization may also be used to measure the differential expression of a plurality of biomarkers. This method permits the localization of mRNAs of interest in the cells of a tissue section. For this method, the tissue may be frozen, or fixed and embedded, and then cut into thin sections, which are arrayed and affixed on a solid surface. The tissue sections are incubated with a labeled antisense probe that will hybridize with an mRNA of interest. The hybridization and washing steps are generally performed under highly stringent conditions. The probe may be labeled with a fluorophore or a small tag (such as biotin or digoxigenin) that may be detected by another protein or antibody, such that the labeled hybrid may be detected and visualized under a microscope. Multiple mRNAs may be detected simultaneously, provided each antisense probe has a distinguishable label. The hybridized tissue array is generally scanned under a microscope. Because a sample of tissue from a subject with cancer may be heterogeneous, i.e., some cells may be normal and other cells may be cancerous, the percentage of positively stained cells in the tissue may be determined. This measurement, along with a quantification of the intensity of staining, may be used to generate an expression value for each biomarker.

The number of biomarkers whose expression is measured in a sample of cells from a subject with cancer may vary. Since the predicted score of survival is based upon the differential expression of the biomarkers, a higher degree of accuracy should be attained when the expression of more biomarkers is measured. In a preferred embodiment, the expression of at least all 64 of the biomarkers will be measured. As demonstrated in Examples 5 and 6, risk classifications based upon the differential expression of the 64 biomarkers were from about 87% to 100% accurate. In another embodiment, the differential expression of at least about 55, at least about 50, at least about 45, or at least about 40 biomarkers may be measured. In yet another embodiment, the differential expression of at least about 35, at least about 30, or at least about 25 biomarkers may be measured. In still another embodiment, the differential expression of at least about 20 biomarkers may be measured.

(c) Obtaining a Sample of Cells from a Subject with Cancer

The expression of a plurality of biomarkers will be measured in a sample of cells from a subject with cancer. The type and classification of the cancer can and will vary. The cancer may be an early stage cancer, i.e., stage I or stage II, or it may be a late stage cancer, i.e., stage III or stage IV. The cancer may be a cancer of the lung. The lung cancer may be a non-small cell lung cancer (NSCLC), which includes squamous cell carcinoma, adenocarcinoma, and large cell carcinoma. Other types of cancer include, but are not limited to, bladder cancer, bone cancer, brain cancer, breast cancer, cervical cancer, colon cancer, duodenal cancer, endometrial cancer, esophageal cancer, eye cancer, gallbladder cancer, head and neck cancer, liver cancer, larynx cancer, small cell lung cancer, lymphomas, melanoma, mouth cancer, ovarian cancer, pancreatic cancer, penal cancer, prostate cancer, rectal cancer, renal cancer, skin cancer, testicular cancer, thyroid cancer, and vaginal cancer.

Generally, the sample of cells or tissue sample will be obtained from the subject with cancer by biopsy or surgical resection. The type of biopsy can and will vary, depending upon the location and nature of the cancer. A sample of cells, tissue, or fluid may be removed by needle aspiration biopsy. For this, a fine needle attached to a syringe is inserted through the skin and into the organ or tissue of interest. The needle is typically guided to the region of interest using ultrasound or computed tomography (CT) imaging. Once the needle is inserted into the tissue, a vacuum is created with the syringe such that cells or fluid may be sucked through the needle and collected in the syringe. A sample of cells or tissue may also be removed by incisional or core biopsy. For this, a cone, a cylinder, or a tiny bit of tissue is removed from the region of interest. CT imaging, ultrasound, or an endoscope is generally used to guide this type of biopsy. Lastly, the entire cancerous lesion may be removed by excisional biopsy or surgical resection.

Once a sample of cells or sample of tissue is removed from the subject with cancer, it may be processed for the isolation of RNA or protein using techniques well known in the art and disclosed in standard molecular biology reference books, such as Ausubel et al., (2003) Current Protocols in Molecular Biology, John Wiley & Sons, New York, N.Y. A sample of tissue may also be stored in RNAlater (Ambion; Austin Tex.) or flash frozen and stored at −80° C. for later use. The biopsied tissue sample may also be fixed with a fixative, such as formaldehyde, paraformaldehyde, or acetic acid/ethanol. The fixed tissue sample may be embedded in wax (paraffin) or a plastic resin. The embedded tissue sample (or frozen tissue sample) may be cut into thin sections. RNA or protein may also be extracted from a fixed or wax-embedded tissue sample.

The subject with cancer will generally be a mammalian subject. Mammals may include primates, livestock animals, and companion animals. Primates may include humans, New World monkeys, Old World monkeys, gibbons, and great apes. Livestock animals may include horses, cows, goats, sheep, deer (including reindeer) and pigs. Companion animals may include dogs, cats, rabbits, and rodents (including mice, rats, and guinea pigs). In an exemplary embodiment, the subject is a human.

(d) Generating a Risk Score

The biomarkers of this invention are related to cancer survival. The differential patterns of expression of a plurality of these biomarkers may be used to predict the survival outcome of a subject with cancer. Certain biomarkers tend to be over-expressed in long-term survivors, whereas other biomarkers tend to be over-expressed in short-term survivors. The unique pattern of expression of a plurality of biomarkers in a subject (i.e., the expression signature) may be used to generate a risk score of survival. Subjects with a high risk score may have a short survival time (<2 years) after surgical resection. Subjects with a low risk score may have a longer survival time (>5 years) after resection.

Regardless of the technique used to measure the differential expression of a plurality of biomarkers (detailed in section (I)(b)), the expression of each biomarker typically will be converted into an expression value. These expression values then will be used to calculate a risk score of survival for a subject with cancer using statistical methods well known in the art. The risk scores may be calculated using a principal components analysis. The risk scores may also be calculated using a univariate Cox regression analysis. In a preferred embodiment, the risk scores may be calculated using a partial Cox regression analysis.

The scores generated by a partial Cox regression analysis fall into two groups: 1) those having a positive value (e.g., 0.011, and 0.581); and 2) those having a negative value (e.g., −0.006 and −0.255). A risk score having a positive value is associated with a short survival time, and a risk score having a negative value is associated with a long survival time. As shown in Examples 5 and 6, the risk scores generated by a partial Cox regression analysis based upon the patterns of expression of the 64 biomarkers of the invention have a high degree of predictive accuracy, from about 87% to 100%.

Thus, risk scores based upon the expression of 64 biomarkers may be accurate about 90% of the time. Risk scores based upon the expression of fewer than 64 biomarkers may have a lower percent of accuracy, such as about 85%, about 80%, about 75%, about 70%, about 65%, or about 60%. While the degree of accuracy may depend upon the absolute number of biomarkers, it may also depend upon the degree of correlation between the biomarker and cancer survival.

In a preferred embodiment of this method, a tissue sample may be removed by surgical resection from a subject with an early stage NSCLC. The sample of tissue may be stored in RNAlater or flash frozen, such that RNA may be isolated at a later date. The RNA may be used as template for QRT-PCR in which the expression of a plurality of biomarkers is analyzed, and the expression data are used to derive a risk score using the partial Cox regression classification method. The risk score may be used to predict whether the subject will be a short-term or a long-term cancer survivor.

In an especially preferred embodiment of this method, a sample of tissue may be collected from a subject with an early stage NSCLC. RNA may be isolated from the tissue and used to generate labeled probes for a nucleic acid microarray analysis. The expression values generated from the microarray analysis may be used to derive a risk score using the partial Cox regression classification method. The risk score may be used to predict whether the subject will be a short-term or a long-term cancer survivor.

(II) Method for Determining the Prognosis of a Subject with Cancer

Another aspect of the invention provides a method for determining the prognosis of a subject with a cancer. The method comprises measuring the differential expression of a plurality of biomarkers in a sample of cells from the subject. The differential expression of each biomarker is converted into an expression value, and the expression values are used to derive a score for that subject using a statistical method, as detailed above. A score having a positive value is indicative of a poor prognosis or a poor outcome, whereas a score having a negative value is indicative of a good prognosis or a good outcome.

In a preferred embodiment of this method, an expression signature for a subject with an early stage NSCLC is generated by nucleic acid microarray analysis, and the expression values are used to calculate a score. The calculated score may be used to predict whether the subject will have a good prognosis or a poor prognosis of cancer outcome.

(III) Method for Selecting a Treatment for a Subject with Cancer

A further aspect of the invention provides a method for selecting an effective treatment for a subject with cancer. Once a risk score has been calculated (see above) for a subject, that information may be used to decide upon an appropriate course of treatment for the subject. A subject having a positive risk score (i.e., short survival time or poor prognosis) may benefit from an aggressive therapeutic regime. An aggressive therapeutic regime may comprise the appropriate chemotherapy agent or agents. An aggressive therapeutic regime may also comprise radiation therapy. The treatment regime can and will vary, depending upon the type and stage of cancer. A subject having a negative risk score (i.e., long survival time or good prognosis) may not need additional treatment, since the subject is not likely to develop a recurrent cancer.

In a preferred embodiment of this method, the cancer to be treated may be an early stage non-small cell lung cancer (NSCLC). The NSCLC may be a squamous cell carcinoma. The NSCLC may be an adenocarcinoma. The NSCLC may be a large cell carcinoma.

(IV) A Plurality of Biomarkers

Another aspect of the invention is the provision of a plurality of biomarkers whose differential patterns of expression in a cancer cell may be used to predict cancer survival, cancer outcome, or cancer prognosis. The unique set of biomarkers of this invention is presented in Table A.

(V) Kit for Predicting Survival or Prognosis of a Subject with Cancer

A further aspect of the invention provides kits for predicting survival or prognosis of a subject with cancer. A kit comprises a plurality of agents for measuring the differential expression of a plurality of biomarkers, means for converting the expression data into expression values, and means for analyzing the expression values to generate scores that predict survival or prognosis. The agents in the kit for measuring biomarker expression may comprise an array of polynucleotides complementary to the mRNAs of the biomarkers. In another embodiment, the agents in the kit for measuring biomarker expression may comprise a plurality of PCR probes and/or primers for QRT-PCR. Possible means for converting the expression data into expression values and for analyzing the expression values to generate scores that predict survival or prognosis are described in the examples below.

(VI) Nucleic Acid Array

Another aspect of the invention provides for a nucleic acid array comprising polynucleotides that hybridize to the mRNAs of biomarkers of the invention. Generally speaking, the nucleic acid array is comprised of a substrate having at least one address. Nucleic acid arrays are commonly known in the art, and moreover, substrates that comprise nucleic acid arrays are also well known in the art. Non-limiting examples of substrate materials include glass and plastic. A substrate may be shaped like a slide or a chip (i.e. a quadrilateral shape), or alternatively, a substrate may be shaped like a well.

The array of the present invention is comprised of at least one address, wherein the address has disposed thereon a nucleic acid that can hybridize to the mRNA of a biomarker of the invention. In one embodiment, the array is comprised of at least 20, at least 25, at least 30, at least 35, at least 40, at least 45, at least 50, at least 55, at least 60, or at least 64 addresses, wherein each address has disposed thereon a nucleic acid that can hybridize to the mRNA of a biomarker for predicting survival of a subject with a lung cancer. In another embodiment, the array comprises at least 64 addresses, wherein each address has disposed thereon a nucleic acid that can hybridize to the mRNA of a different biomarker selected from the group of biomarkers comprising APC, ARHGEF1, BCL2, CASP10, CASP8, CCR2, CDH8, DTNA, ENPP2, FUCA1, GNAT2, GOLGA1, IL8RB, ITSN1, MAP4K1, MEF2C, MLLT10, NR1H4, NTRK3, PBP, PIGC, PIK3R1, PKNOX1, PPDX, PRKACA, RAB28, RAE1, SNX1, SON, TMSB4X, TRA2A, ZNFN1A1, ABCC1, ADAM17, ARL4A, BIK, BLM, CHERP, CRABP1, DSP, FBN2, GLI2, HNRPD, INHA, IRS1, LARS2, LY6D, NID, NOTCH3, PCDHGA12, PFN2, PLEC1, PSEN1, PYGL, SLC2A1, SLC7A1, SMC1L1, SMARCA3, STC1, UPK2, VGLL1, ZNF154, ZNF410, and ZWINTAS. In each of the above embodiments, the array may also comprise one or more addresses wherein the address has disposed thereon a control nucleic acid. The control may be an internal control (i.e. a control for the array itself) and/or an external control (i.e. a control for the sample applied to the array).

An array typically is comprised from between about 1 to about 10,000 addresses. In one embodiment, the array is comprised from between about 10 to about 8,000 addresses. In another embodiment, the array is comprised of no more than 500 addresses. In an alternative embodiment, the array is comprised of no less than 500 addresses.

Methods of using nucleic acid arrays are well known in the art.

DEFINITIONS

The term "array" is used interchangeably with the term "microarray" herein.

The term "cancer," as used herein, refers to the physiological condition in mammals that is typically characterized by unregulated cell proliferation, and the ability of those cells to invade other tissues.

A "carcinoma" is a cancer that arises from epithelial cells.

The term "expression," as used herein, refers to the conversion of the DNA sequence information into messenger RNA (mRNA) or protein. Expression may be monitored by measuring the levels of full-length mRNA, mRNA fragments, full-length protein, or protein fragments.

The phrase "gene expression signature," as used herein refers to the unique pattern of gene expression in a cell, and in particular, a cancer cell.

The term "hybridization," as used herein, refers to the process of binding, annealing, or base-pairing between two single-stranded nucleic acids. The "stringency of hybridization" is determined by the conditions of temperature and ionic strength. Nucleic acid hybrid stability is expressed as the melting temperature or $T_m$, which is the temperature at which the hybrid is 50% denatured under defined conditions. Equations have been derived to estimate the $T_m$ of a given hybrid; the equations take into account the G+C content of the nucleic acid, the length of the hybridization probe, etc. (e.g., Sambrook et al, 1989, chapter 9). To maximize the rate of annealing of the probe with its target, hybridizations are generally carried out in solutions of high ionic strength (6×SSC or 6×SSPE) at a temperature that is about 20-25° C. below the $T_m$. If the sequences to be hybridized are not identical, then the hybridization temperature is reduced 1-1.5° C. for every 1% of mismatch. In general, the washing conditions should be as stringent as possible (i.e., low ionic strength at a temperature about 12-20° C. below the calculated $T_m$). As an example, highly stringent conditions typically involve hybridizing at 68° C. in 6×SSC/5×Denhardt's solution/1.0% SDS and washing in 0.2×SSC/0.1% SDS at 65° C. The optimal hybridization conditions generally differ between hybridizations performed in solution and hybridizations using immobilized nucleic acids. One skilled in the art will appreciate which parameters to manipulate to optimize hybridization.

The term "nucleic acid," as used herein, refers to sequences of linked nucleotides. The nucleotides may be deoxyribonucleotides or ribonucleotides, they may be standard or non-standard nucleotides; they may be modified or derivatized nucleotides; they may be synthetic analogs. The nucleotides may be linked by phosphodiester bonds or non-hydrolyzable bonds. The nucleic acid may comprise a few nucleotides (i.e., oligonucleotide), or it may comprise many nucleotides (i.e., polynucleotide). The nucleic acid may be single-stranded or double-stranded.

The term "prognosis," as used herein refers to the probable course and outcome of a cancer, and in particular, the likelihood of recovery.

As various changes could be made in the above compounds, methods, and products without departing from the scope of the invention, it is intended that all matter contained in the above description and in the examples given below, shall be interpreted as illustrative and not in a limiting sense.

EXAMPLES

The following examples illustrate, in part, the methods used to identify the 64 lung cancer survival genes, methods to validate their use as biomarkers, and methods to confirm their predictive power.

Example 1

Identification of Lung Cancer-Survival Related Genes

There have been several studies using microarray technology that were performed to determine genetic profiles predictive of cancer survival in NSCLC to develop nonpathological methods for stratifying risk (Beer et al., 2002, Nat Med 8:816-824; Sun et al., 2004, Mol Cancer 3:35; Wigle et al., 2002 Cancer Res 62:3005-3008; Borczuk et al., 2004, Am J Respir Grit Care Med 170:167-174). However, the survival-related genes identified in these studies lacked similarities due to limited patient samples, disease heterogeneity and some technical factors such as different microarray platforms and specimen processing. In this study, a meta-analysis of five data sets was conducted to search for differentially expressed genes related to survival time (less than 2 years and greater than 5 years).

Samples from Washington University in St. Louis. Thirty-six patients who underwent resection of stage 1B NSCLC at Washington University School of Medicine (WUSM) were recruited for this study. These samples are referred to as dataset 1. Informed consent was obtained from the patients for tissue procurement prior to surgery and their medical records were maintained according to institutional guidelines and in conformance with HIPPA regulations. The overall survival data on all patients were censored on the date of the last follow-up visit or death from causes other than lung cancer. Tumor tissues were processed by the Human Tissue Bank and the Gene Chip Facility at WUSM according to standard operating procedures and protocols. Briefly, frozen tissue samples at −80° C. were pulverized and total cellular RNA was collected from each flash frozen sample using TRIzol RNA isolation reagent (Invitrogen, Gaithersburg, Md.). Total RNA was processed with a Qiagen RNeasy Mini kit. In vitro transcription-based RNA amplification was then performed on at least 8 micrograms of total RNA from each sample. Complementary DNA was synthesized using the commercially-available T7-(dT)24 primer. The cDNA was processed using phase-lock gel (Fisher Cat ID E0032005101) phenol/chloroform extraction. Next, in vitro transcriptional labeling with biotin was performed using the Enzo 'Bioarray Kit' (Affymetrix Cat ID 900182). The resulting cRNA was processed again using the Qiagen RNeasy Mini kit (QIAGEN, Valencia, Calif.). Labelled cRNA was hybridized to HG_U95Av2 (Affymetrix, Santa Clara, Calif.) arrays according to manufacturer's instructions. The raw fluorescence intensity data within CEL files were preprocessed with the Robust Multichip Average (RMA) algorithm (Irizarry et al., 2003, Nucl Acids Res 31:e15), as implemented with R packages from Bioconductor (www.bioconductor.org). This algorithm analyzes the microarray data in three steps: background adjustment, quantile normalization, and finally summation of the probe intensities for each probe set using a log scale linear additive model for the log transform of (background corrected, normalized) PM intensities.

Samples from Mayo Clinic. Eighteen patients with stage I squamous cell carcinoma (SCC) were selected from the patients diagnosed with lung cancer from 1997 to 2001 who underwent curative resection at Mayo Clinic, Minnesota, USA. These samples are referred to as dataset 2. All enrolled patients and use of their tissues in the study were approved by the institutional review board of Mayo Clinic. The resected tumors were flash frozen to −80° C. within 30 minutes after the tissues were surgically removed. The RNA isolation, cRNA synthesis and microarray hybridization were performed as described by Sun et al. (2004, Mol Cancer 3:35). The raw fluorescence intensity data within CEL files were also preprocessed with the RMA algorithm.

Samples from other groups. Dataset 3 was from Beer et al. (2002, Nat Med 8:816-824) which included 67 stage I primary lung adenocarcinomas (http//dot.ped.med.umich.edu:2000/ourimage/pub/Lung/index.html). Dataset 4 was from Borczuk et al. (2004, Am J Respir Crit Care Med 170:167-174), which included one squamous and three adenocarcinomas (http://hora.cpmc.columbia.edu/dept/pulmonary/5ResearchPages/Laboratories/powell%20supp1.htm). Dataset 5 was from Bhattacharjee et al. (2001, Proc Natl Acad Sci USA 98:13790-13795) and included 72 stage I lung adenocarcinomas (www.broad.mit.edu/mpr/lung/). The raw data within the CEL files of these datasets were also preprocessed with the RMA algorithm.

Details of the clinical information for the subjects in each dataset are described in Table 1. Datasets 6 and 7 were used for confirmation (see Example 6).

TABLE 1

| Clinical summary of patients in the analyzed datasets | | | | | | | |
|---|---|---|---|---|---|---|---|
| | Dataset 1 | Dataset 2 | Dataset 3 | Dataset 4 | Dataset 5 | Dataset 6 | Dataset 7 |
| Total number of samples | 36 | 18 | 67 | 4 | 72 | 63 | 64 |
| Mean age (range) | 66 (48-81) | 70 (59-80) | 64 (41-85) | 76 (61-88) | 64 (33-88) | 65 (40-82) | — |
| Sex | | | | | | | |
| Male | 20 | 10 | 25 | 2 | 29 | 27 | — |
| Female | 16 | 8 | 42 | 2 | 43 | 36 | — |

TABLE 1-continued

Clinical summary of patients in the analyzed datasets

|  | Dataset 1 | Dataset 2 | Dataset 3 | Dataset 4 | Dataset 5 | Dataset 6 | Dataset 7 |
|---|---|---|---|---|---|---|---|
| Mean follow-up (days) | | | | | | | |
| Total overall survival | 1369 | 1301 | 1310 | 303 | 1403 | 1387 | 1139 |
| Alive | 1570 | 1813 | 1430 | 303 | 1805 | 1441 | 1414 |
| Deceased | 665 | 660 | 924 | — | 901 | 1064 | 785 |
| Stage | | | | | | | |
| IA | 0 | 7 | 44 | 1 | 33 | 25 | 30 |
| IB | 36 | 11 | 23 | 3 | 39 | 38 | 27 |
| Histological type | | | | | | | |
| ADC | 14 | 0 | 67 | 3 | 72 | 63 | 31 |
| SCC | 18 | 18 | 0 | 1 | 0 | 0 | 33 |
| Others | 4 | 0 | 0 | 0 | 0 | 0 | 0 |

Gene matching. Because several different microarray platforms were used in these datasets, the probe sets were corresponded and standardized. The batch query tool provided by Affymetrix (www.affymetrix.com/analysis/netaffx/batch_query.affx) was used for the correspondence between probe sets of the datasets (Liu et al., 2003, Nucl Acids Res 31:82-86). Based on the latest UniGene clusters annotation provided by the manufacturer (NCBI Build 35.1), there were a total of 4905 genes on all the five Affymetrix microarray systems HG_U95Av2, Hu6800, Hu133A, HG_U133AB, and Hu133 plus2.

Distance Weighted Discrimination (DWD). Systematic differences from different datasets were very significant, which would compromise the integrity of the data from the different laboratories. To integrate the gene expression data from datasets 1 to 5, the Distance Weighted Discrimination (DWD) method (//genome.unc.edu/pubsup/dwd/index.html) (Benito et al., 2004, Bioinformatics 20:105-114) was used to identify and adjust systematic differences that were present within these microarray data sets. All of the 197 samples from the five datasets were broken into two sub-branches according to disease status, each of which was composed of samples from all of the five datasets. Poolability tests were performed, and the data resources were randomly reshuffled to generate 100 replicates of simulated data. The number of p-values below some certain thresholds were compared with the expected counts obtained by simulations that took into account the distributions of the DWD-transformed gene expression data and sample size.

Data Analysis. ANOVA analysis was applied to 88 patients who survived less than 2 years or survived more than 5 years after surgery in datasets 1 to 5 to preselect survival-related genes. 10,000 permutation tests were performed to obtain empirical p-values for each gene. Genes with significant survival effects ($P<0.01$) were selected for Cox proportional hazards regression analyses. Multivariate Cox proportional hazards regression analyses (adjusted for age, gender, cancer subtype and cancer stage) with 10000 bootstrap resampling approach were performed for each survival-related gene using all of 197 samples in datasets 1 to 5. The genes were ranked according to the bootstrap frequencies of $P<0.01$ for its gene expression in regression models.

Hierarchical clustering based on the centered Pearson correlation coefficient algorithm and the average linkage method were used to show the expression patterns of survival-related genes in dataset 1 to 5. All of the data analyses were implemented using the R statistical package (Ihaka and Gentleman 1996, J Comput Graph Statist 5:299-314).

Results. The DWD method was used to correct for systematic biases across the microarray batches. The hierarchical cluster analysis using the original non-transformed data classified the samples into five distinct groups according to the data sources rather than disease status, demonstrating large systematic biases among the five studies. After DWD adjustment, however, all of the 197 samples from the five datasets were clustered into two subbranches according to the disease status rather than data sources. Each of the subbranches was composed of samples from all of the five datasets. Thus, the batch differences were eliminated. Poolability tests revealed that the DWD transformed gene-expression data from different resources were poolable.

A three-way ANOVA was used to filter genes potentially contributing to survival in a subset of data with survival time less than 2 years or more than 5 years. Then, the multivariate Cox proportional hazards regression analysis was applied to choose genes for constructing the partial Cox regression predictive components. The proportional hazards assumption for variables such as age, gender, cancer subtype and cancer stage was investigated by examining the scaled Schoenfeld residuals. Gender and cancer stage generally displayed a significant deviation from the proportional hazards assumption. Therefore, these two variables were taken as strata and others as covariates in the Cox proportional hazards model. A plot of global P values from testing the proportional hazards assumption for all the survival-related genes revealed the model used in this survival analysis was statistically warranted. In the Cox regression analysis, 10,000 time bootstraps were used to determine the validity of the chosen genes in the construction of regression components.

This meta-analysis identified 124 differentially expressed genes that are associated with overall cancer survival ($P<0.01$) (Table 2). Most of these survival genes are related to cell adhesion, cell motility, cell proliferation and apoptosis. Relatively consistent changes were observed for both genes whose expression was higher in low-risk patients than in high-risk patients and genes whose expression was higher in high-risk patients than in low-risk patients. Since data from normal paired lungs were not used in these analyses, it is not clear if these genes were all overexpressed in both low-risk and high-risk patients. Therefore, there are at least four possibilities: 1) one group of genes overexpressed in low risk patients and another group of genes overexpressed in high risk patients; 2) one group of genes overexpressed in high risk patients and another group of genes underexpressed in high risk patients; 3) one group of genes overexpressed in low risk patients and another group of genes underexpressed in low risk patients; or 4) a mixture of all three scenarios.

TABLE 2

Genes related to survival

| Gene | Function | P-value | Gene | Function | P-value |
|---|---|---|---|---|---|
| *Over-expressed in low risk patents* | | | | | |
| AB12 | Cell Migration | 0.0023 | CCR2 | C-C chemokine receptor activity | 0.0001 |
| APC | Cell Adhesion | 0.0037 | | | |
| ARHGEF1 | Cell Proliferation | 0.0031 | CDC2L5 | Positive regulation of cell proliferation | 0.0044 |
| BCL2 | Anti-apoptosis | 0.0002 | | | |
| BNIP1 | Anti-apoptosis | 0.0004 | CUGBP2 | Nuclear mRNA splicing, via spliceosome | 0.0045 |
| C21orf33 | Cell wall | 0.0080 | | | |
| CASP10 | Inoduction of apoptosis | 0.0082 | DBH | Catecholamine biosynthesis | 0.0031 |
| | | | FLT3 | Positive regulation of cell proliferation | 0.0067 |
| CASP8 | Regulation of apoptosis | 0.0070 | | | |
| | | | FUCA1 | Carbohydrate metabolism | 0.0026 |
| CDH8 | Cell adhesion | 0.0007 | GALGT | Carbohydrate metabolism | 0.0014 |
| CHRNA2 | Signal transduction | 0.0100 | GCS1 | Carbohydrate metabolism | 0.0044 |
| DPH2L1 | Cell proliferation | 0.0049 | GGCX | Gamma-glutamyl carboxylase activity | 0.0034 |
| DTNA | Signal transduction | 0.0003 | | | |
| DYRK1A | Transferase activity | 0.0019 | GLG1 | Fibroblast growth factor binding | 0.0100 |
| ENPP2 | Cell motility, chemotaxis | 0.0036 | | | |
| | | | GM2A | Sphingolipid catabolism | 0.0100 |
| GOLGA1 | Golgi autoantigen | 0.0079 | GNAT2 | G-protein coupled receptor protein signaling pathway | 0.0027 |
| GPLD1 | Cell-matrix adhesion | 0.0037 | | | |
| IL8RB | Cell motility, chemotaxis | 0.0090 | GNRH1 | Negative regulation of cell proliferation | 0.0083 |
| ITGB3 | Cell-matrix adhesion | 0.0052 | GTF21 | Transcription factor activity | 0.0042 |
| ITSN1 | Calcium ion binding | 0.0010 | INSR | Epidermal growth factor receptor activity | 0.0070 |
| LST1 | Immune response | 0.0090 | | | |
| MAPK14 | MAP kinase activity | 0.0081 | MAP4K1 | MAP kinase kinase kinase kinase activity | 0.0060 |
| NIFUN | Metal ion binding | 0.0066 | | | |
| NNT | Electron transport | 0.0070 | MAPK10 | MAP kinase kinase activity | 0.0090 |
| NTRK3 | Cell differentiation | 0.0048 | MEF2C | Transcription factor activity | 0.0032 |
| PPOX | Electon transport | 0.0030 | MLLT10 | Transcription factor activity | 0.0016 |
| PTGER3 | Cell death | 0.0080 | NFATC3 | Transcription factor activity | 0.0090 |
| RAB28 | GTPase activity | 0.0044 | NR1H4 | Transctiption factor activity | 0.0000 |
| RAD9A | Regulation of cell cycle | 0.0075 | PBP | Serine-type endopeptidase inhibitor activity | 0.0059 |
| RAE1 | Cytoskeleton | 0.0021 | PIGC | Transferase activity, transferring glycosyl groups | 0.0100 |
| RBPMS | RNA processing | 0.0070 | | | |
| SELL | Cell motility | 0.0060 | PIK3R1 | Phosphatidylinositol 3-kinase activity | 0.0050 |
| SLC15A1 | Oligopeptide transport | 0.0080 | | | |
| | | | PKNOX1 | Transcription factor activity | 0.0031 |
| SLC17A4 | Sodium ion transport | 0.0100 | PRKACA | cAMP-dependent protein kinase activity | 0.0001 |
| SON | Anti-apoptosis | 0.0027 | | | |
| SUOX | Metal ion binding | 0.0070 | RPS14 | Structural constituent of ribosome | 0.0073 |
| TIAL1 | Induction of apoptosis | 0.0060 | | | |
| | | | SAA4 | Lipid transporter activity | 0.0044 |
| UBE21 | Ubiquitin cycle | 0.0040 | SLC35B1 | UDP-galactose transporter activity | 0.0080 |
| | | | SNX1 | Intracellular protein transport | 0.0055 |
| | | | SSR2 | Cotranslational protein-membrane targeting | 0.0046 |
| | | | SUPT4H1 | Positive regulation of transcription | 0.0003 |
| | | | TMED9 | Intracellular protein transport | 0.0059 |
| | | | TMSB4X | Regulation of actin cytoskeleton | 0.0027 |
| | | | TRA2A | Nuclear mRNA splicing, via spliceosome | 0.0000 |
| | | | ZNFN1A1 | Regulation of transcription, DNA-dependent | 0.0002 |
| *Over-expressed in high risk patients* | | | | | |
| ABCA2 | ATPase activity | 0.0024 | ARL4A | Small GTPase mediated signal transduction | 0.0012 |
| ABCC1 | Response to drug | 0.0001 | | | |
| ADAM17 | Cell-cell signaling | 0.0020 | BIK | Induction of apoptosis | 0.0040 |
| BLM | DNA repair | 0.0100 | CBX3 | Regulation of transcription, DNA-dependent | 0.0090 |
| C4orf10 | | 0.0071 | | | |
| CHERP | Neurogenesis | 0.0013 | DSP | Cell-cell adherens junction | 0.0020 |
| CRABP1 | Signal transduction | 0.0100 | ETV6 | Transcription factor activity | 0.0088 |
| HMGB2 | DNA Repair | 0.0090 | FBN2 | Extracellular matrix structural constituent | 0.0083 |
| INHA | Induction of apoptosis | 0.0083 | | | |
| | | | GABRA3 | Gamma-aminobutyric acid signaling pathway | 0.0045 |
| LY6D | Cell adhesion | 0.0100 | | | |
| NID | Cell-matrix adhesion | 0.0009 | GLI2 | Transcription factor activity | 0.0085 |
| | | | HNRPD | Regulation of transcription, DNA-dependent | 0.0031 |
| NOTCH3 | Cell differentiation | 0.0011 | | | |
| PCDHGA12 | Cell adhesion | 0.0023 | IRS1 | Insulin receptor binding | 0.0072 |

TABLE 2-continued

Genes related to survival

| Gene | Function | P-value | Gene | Function | P-value |
|---|---|---|---|---|---|
| PFN2 | Actin cytoskeleton | 0.0074 | LARS2 | Leucine-tRNA ligase activity | 0.0020 |
| PSEN1 | Anti-apoptosis | 0.0013 | LHCGR | Lutropin-choriogonadotropic hormone receptor activity | 0.0039 |
| RIF1 | ATPase activity | 0.0085 | | | |
| SEMA3F | Extracellular space | 0.0100 | OLFM1 | Latrotoxin receptor activity | 0.0100 |
| SH3GL2 | Transferase activity | 0.0100 | PLEC1 | Structural constituent of cytoskeleton | 0.0030 |
| SMC1L1 | Chromatin binding | 0.0036 | | | |
| STC1 | Cell division | 0.0090 | PPP2R4 | Phosphatase activator activity | 0.0026 |
| SUMO1 | Ubiquitin cycle | 0.0048 | PYGL | Glycogen metabolism | 0.0025 |
| TLK1 | Cell cycle | 0.0068 | SLC2A1 | Carbohydrate transport | 0.0024 |
| TOP3B | DNA modification | 0.0033 | SLC7A1 | Basic amino acid transporter activity | 0.0016 |
| UBE3A | Ubiquitin cycle | 0.0039 | | | |
| UGP2 | Kinase activity | 0.0059 | SMARCA3 | Chromatin modification | 0.0066 |
| ZWINTAS | Cell cycle | 0.0019 | TFAM | DNA-dependent DNA replication | 0.0014 |
| | | | UPK2 | Membrance organization and biogenesis | 0.0055 |
| | | | VARS2 | Translational elongation | 0.0072 |
| | | | VGLL1 | Transcription regulator activity | 0.0032 |
| | | | ZNF154 | Regulation of transcription, DNA-dependent | 0.0044 |
| | | | ZNF410 | Regulation of transcription, DNA-dependent | 0.0004 |

Bold: 64 genes chosen for calculating risk scores of overall survival.

Example 2

Validation of Gene Expression Profiling Using QRT-PCR

To validate the microarray gene expression results from the meta-analysis, the relative expression of nine randomly selected genes associated with overall survival were determined by QRT-PCR analysis using the samples from dataset 1. The nine genes selected for analysis were CRABP1, BLM, ABCC1, SLC2A1, TNFSF4, BCL2, LST1, STC1 and LARS2. Primers for QRT-PCR (Table 3) were designed using Primer Express software version 2.0 (Applied Biosystems, Foster City, Calif.). Amplification of each target DNA was performed with SYBR Green master mix in BIO-RAD Single Color Real-Time PCR Detection system according to the protocols provided. The control gene β-actin and target genes were amplified with equal efficiencies. The method for assessing if two amplicons have the same efficiency is to look at how $\Delta C_T$ ($C_{T,target} - C_{T,\beta\text{-}actin}$, $C_T$ is cycle number at which the fluorescence signal exceeds background) varies with template dilution. The fold change of gene expression in the long-term survival patients relative to the short-term survival patients was calculated as $2^{-\Delta\Delta C_T}$ ($\Delta\Delta C_T = \Delta C_{T\ long} - \Delta C_{T\ short}$). ANOVA was performed to determine differences among the groups. A p-value of less than 0.05 was considered to indicate statistical significance.

TABLE 3

| PCR Primers | | |
|---|---|---|
| Primer | Sequence | SEQ ID NO. |
| β-Actin Forward | CAAGAGATGGCCAGGGCTGCT | 1 |
| β-Actin Reverse | TCCTTCTGCATCCTGTCGGCA | 2 |
| LARS2 Forward | GCCACGGGCGAAAAGC | 3 |
| LARS2 Reverse | CACGTGGGAGGTGCCATAA | 4 |
| BCL2 Forward | CATGTGTGTGGAGAGCGTCAA | 5 |
| BCL2 Reverse | GCCGGTTCAGGTACTCAGTCA | 6 |
| CRABP 1 Forward | GTAGCGGCTGCGTCCAA | 7 |
| CRABP 1 Reverse | CCGTGGTGGATGTCTTGATG | 8 |
| LST1 Forward | TGCTTCTGGCAGTGGTCCTTCT | 9 |
| LST1 Reverse | TCCTCCTTGGTGCCTCTCTTGT | 10 |
| STC1 Forward | CGAGTGGCGGCTCAAAA | 11 |
| STC1 Reverse | CCGCAGCCGACCTGTAGA | 12 |
| TNFSF4 Forward | CATGCAGGCCTAAGTATATGTTGTGT | 13 |
| TNFSF4 Reverse | TGCACCCAAAGCGAGTGA | 14 |
| BLM Forward | CAGAAAGCACCACCCATATGATT | 15 |
| BLM Reverse | GAGGCCAGCATGGTAAGCA | 16 |
| ABCC1 Forward | ATGGTGCCCGTCAATGCT | 17 |
| ABCC1 Reverse | CGATTGTCTTTGCTCTTCATGTG | 18 |
| SLC2A1 Forward | CCTCTCAGTGGCCATCTTTTCT | 19 |
| SLC2A1 Reverse | CCGGCCAAAGCGGTTAA | 20 |

As shown in FIG. 1, there is a high degree of correlation between the QRT-PCR data and the microarray data. Change in expression in the positive direction indicates upregulation in the short-term survival patients and change in expression in the negative direction indicates downregulation in the short-term survival patients.

Example 3

Validation of Gene Expression Profiling Using Tissue Microarray

To determine if increased mRNA levels were correlated with increased protein expression in lung adenocarcinomas from the short-term survival patients, immunohistochemical staining was performed. Lung tissues of 60 stage I NSCLC patients (including 12 patients who survived less than 2 years after surgical resection and 48 who survived for more than 5 years after surgery) were collected during surgery between 1985 and 1999 at the Arthur James Cancer Hospital of the Ohio State University Medical School (OSU; Columbus, Ohio). All tissues were fixed in formalin, and embedded in paraffin. A patient tissue microarray (TMA) was constructed from these tissues for examination of CRABP1 and ABCC1 immunoreactivity in short-term and long-term survival patients. The antigens were retrieved in a vegetable steamer with Dako's TRS, pH 6.1 and antibody staining was performed on the Dako autostainer. Arrays were incubated with antibodies against CRABP1 (Abcam, catalog no. Ab2816, dilution 1:1000) or ABCC1 (=CORA, catalog no. ALX-801-007-C125, dilution 1:50) for 1 hour at RT. Dako's LSAB+ detection kit was used to detect CRABP1, and Vector Lab's Vectastain Elite detection kit used to detect ABCC1. The immunohistochemical staining images were scanned using ImageScope (Aperio Tech. Inc). The percentage of positive cancer cells was scored on a semiquantitative scale as 0 (0%), 1 (1-25%), 2 (25-50%), 3 (50-75% and 4 (75-100%). Intensity was scored as 1 (weak), 2 (intermediate) and 3 (strong). Results are calculated by multiplying the score of percentage of positive cells (P) by the intensity (I). The maximum score is 12. Immunostaining results were evaluated independently by two investigators. Student's t test was used in statistic analysis.

Figure 2:
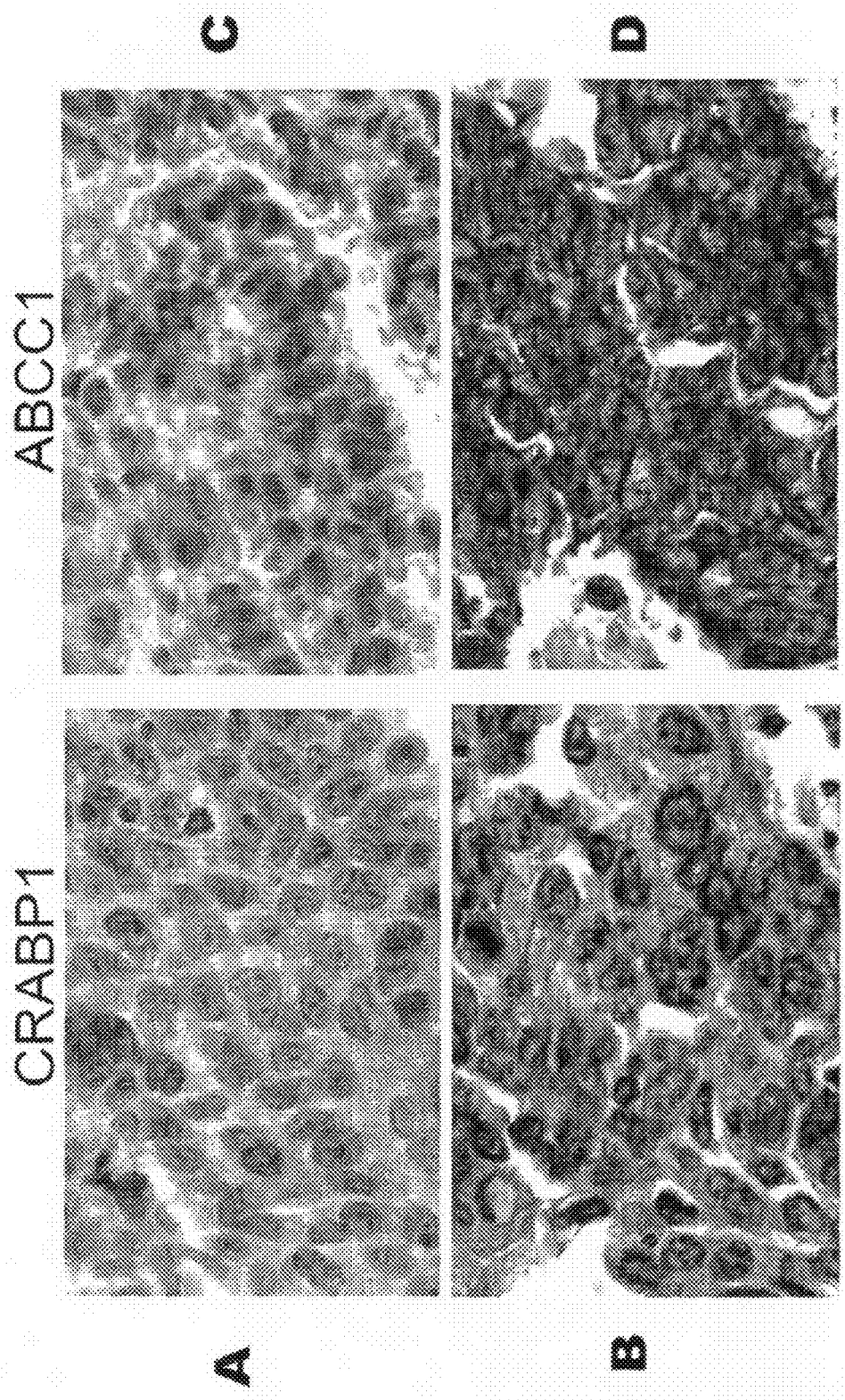
FIG. 2 depicts micrographs illustrating the differential immunostaining of CRABP1 and ABCC1 in long-term survivors (A and C) and short-term survivors (B and D). Positive CRAPB1 immunoreactivity was observed in the cytoplasm of tumor cells from a short-term survivor (B), but not in tumor cells from a long-term survivor (A). Strong membranous ABCC1 staining was observed in tumor cells from a short-term survivor (D), but weak ABCC1 immunoreactivity was found in short-term survivor cells (C).
Figure 3:
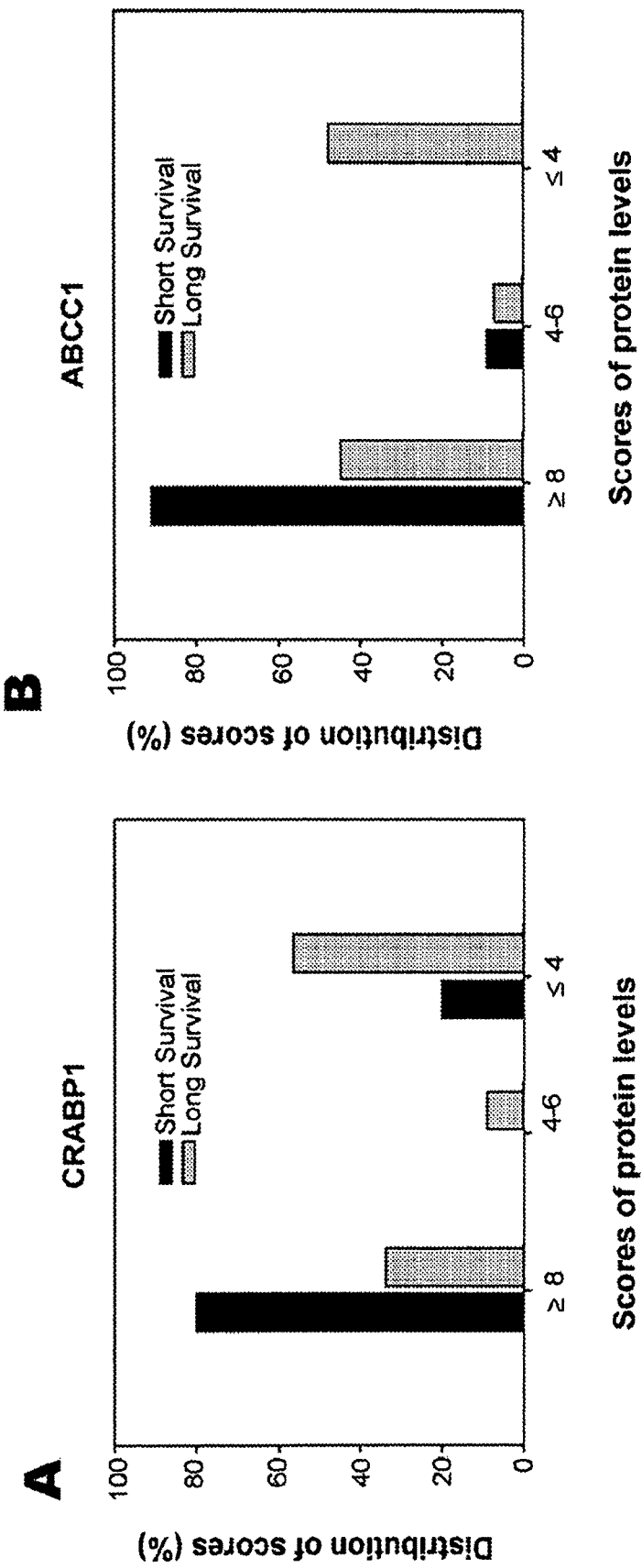
FIG. 3 shows two graphs depicting the distribution of CRABP1 (Panel A) and ABCC1 (Panel B) protein levels in short-term and long-term survival patients. The percentage of positive cancer cells was scored on a semiquantitative scale as 0 (0%), 1 (1-25%), 2 (25-50%), 3 (50-75%), or 4 (75-100%). The intensity of staining was scored as 1 (weak), 2 (intermediate), or 3 (strong). The protein score was calculated by multiplying the positive cell score by the intensity score, with 12 being the maximum score.

TMA revealed that CRABP1 was present in the cytoplasm of tumor cells in most of the lung tumor tissues. CRABP1 exhibited stronger staining in short-term survival patients (FIG. 2B) as compared to long-term survival patients (FIG. 2A). The average staining scores for short and long survivals were 8.8±3.1, and 4.9±2.8 ($p<0.0006$), respectively. In short-term survival patients, 80% and 20% of the samples had scores of 8 ands 4, respectively; while in long-term survival patients, 34% and 59% of the samples had scores 8 and 4, respectively (FIG. 3A). ABCC1 staining was membranous and cytoplasmic in tissues from both sets of NSCLC patients, but the staining was greater in the short-term survivors (FIG. 2C, D). The average staining scores for short-term survival and long-term survival patient tissues were 10±2.3, and 6.6±3.1 ($p<0.002$), respectively (FIG. 3B). In short-term survival patients, 91% and 9% of the samples had scores of $\geq 8$ and $\leq 4$, respectively; while in long survival patients, 45% and 48% of the samples had scores $\geq 8$ and $\leq 4$, respectively. The results indicate that expression of these two proteins is consistent with the results from both microarray and QRT-PCR analyses.

Example 4

Identification of a Gene Expression Signature for Survival

To identify a gene signature predictive of survival outcome, survival analyses were performed based on all of 197 samples in datasets 1 to 5. Partial Cox regression method was performed to construct predictive components and time-dependent receiver operating characteristic curve analysis was applied to evaluate the results (Li and Gui 2004, Bioinformatics 20 Suppl 1:1208-1215). The risk scores were calculated by a linear combination of the gene-expression values for the selected genes, weighted by their estimated regression coefficients. All the samples were classified into high/low risk groups according to the risk scores. To choose an appropriate subset of genes for signature, the following forward selection procedure was carried out: 1) increase one gene each time based on the rank of genes that were identified in the above bootstrap analyses; 2) perform the partial Cox regression analysis and obtain the prediction accuracy using the chosen subset of genes; and 3) repeat steps 1 and 2 until the prediction accuracy is maximized. Kaplan-Meier survival plots and Mantel-Haenszel log rank tests and time-dependent receiver operating characteristic (ROC) analysis were implemented to assess the classification models according the risk scores.

The risk scores were derived from survival analyses of all of 197 samples in datasets 1 to 5 using the partial Cox regression method. The risk scores were estimated with 7 principal components based on the model built by the top 64 survival-related genes shown in bold in Table 2. The risk scores were used to classify the samples into two groups: high risk (positive scores) and low risk (negative scores). Kaplan-Meier survival analyses using expression profiles demonstrated a significantly worse overall survival for high-risk patients compared with low-risk patients ($P=3.2e-13$) (FIG. 4B). In contrast, Kaplan-Meier survival curves based upon cancer stage were able to only distinguish poorer survival of stage IB from stage IA NSCLC ($P=0.032$) (FIG. 4A).

Figure 4A:
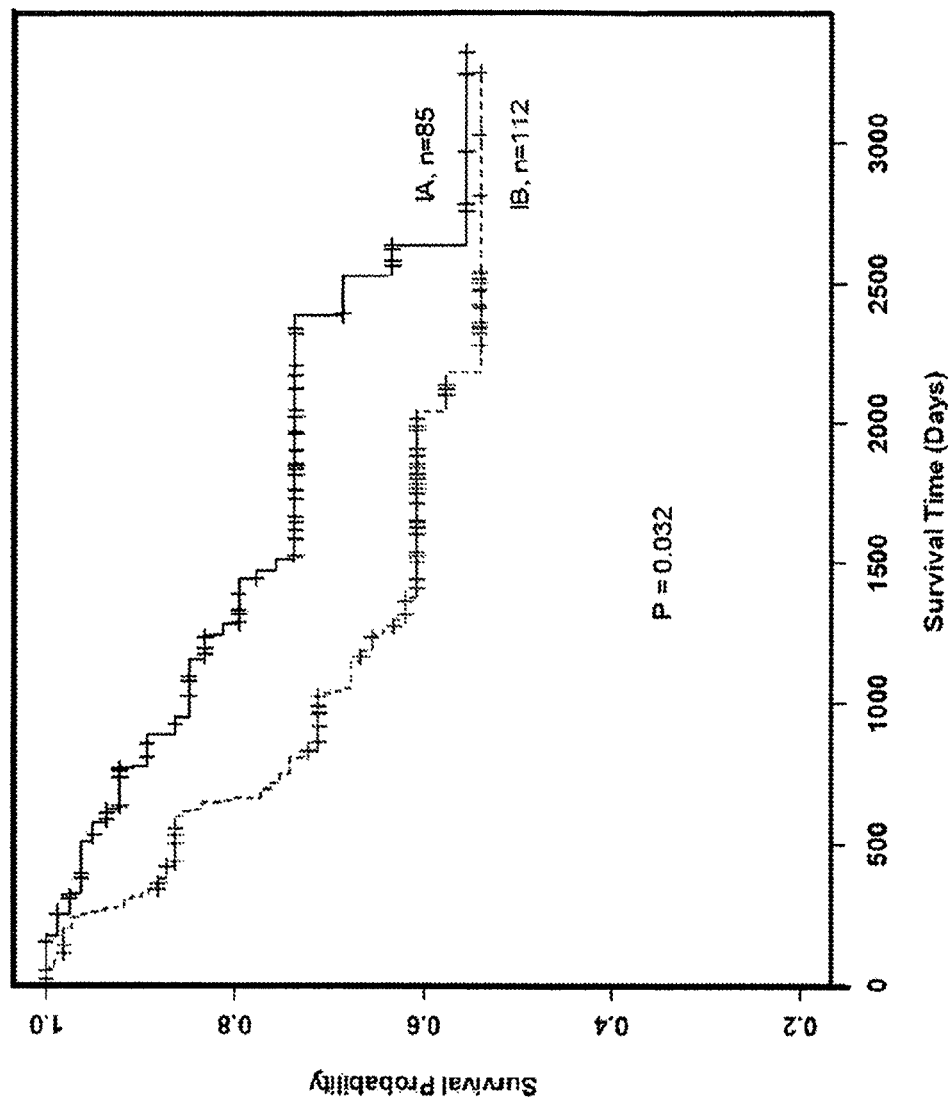
FIG. 4 shows graphs depicting the survival analyses of stage I NSCLC. Panel (A) presents Kaplan-Meier survival curves for two groups of patients with stage IA or IB NSCLC. Panel (B) presents Kaplan-Meier survival curves for stage IA and IB patients classified as having positive (high risk) or negative (low risk) scores based upon the 64-gene expression signature. Panel (C) presents the area under the curve (AUC) for survival models based on stage information (solid line) or expression data (dashed line).
Figure 4B:
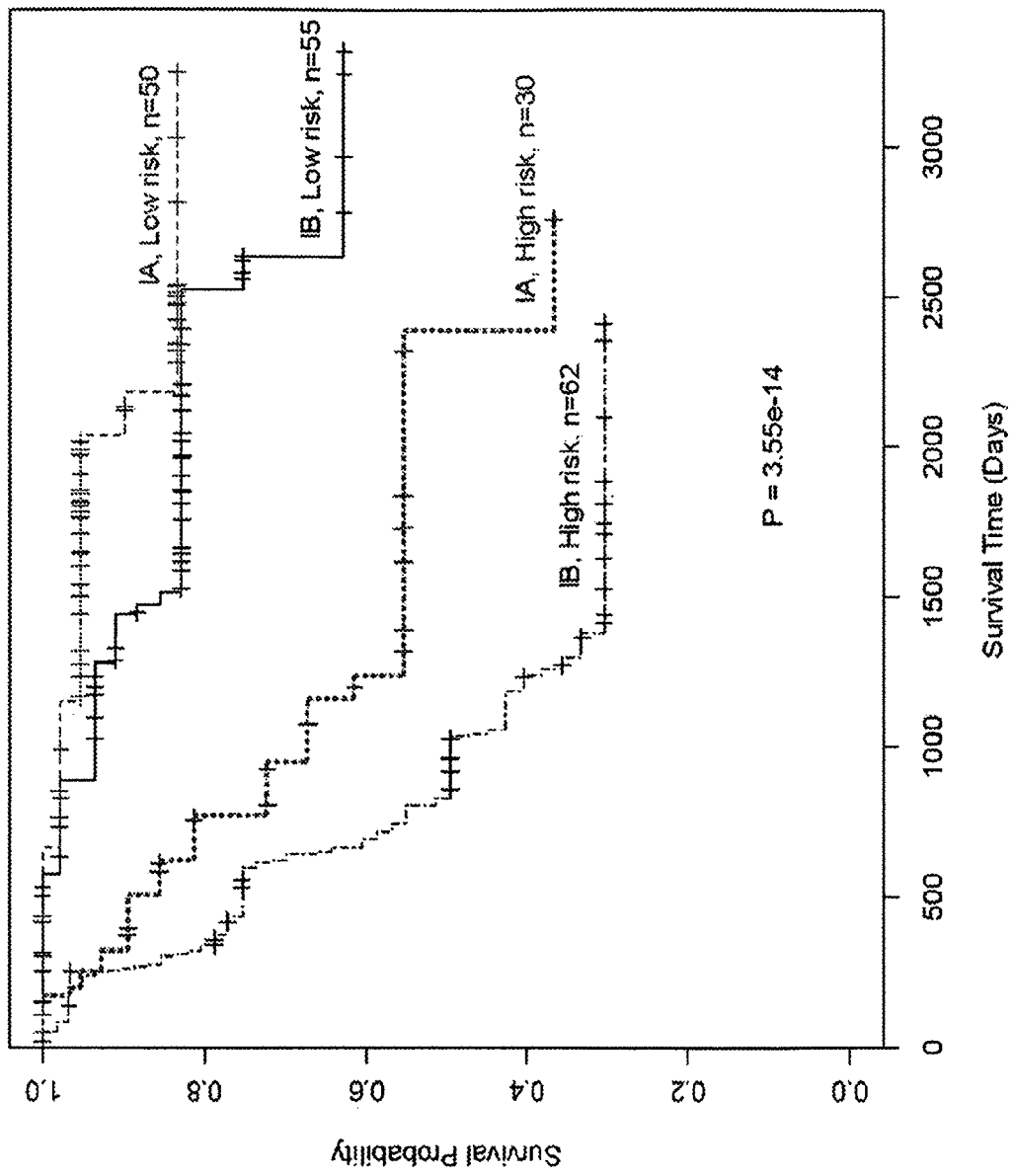
Figure 4C:
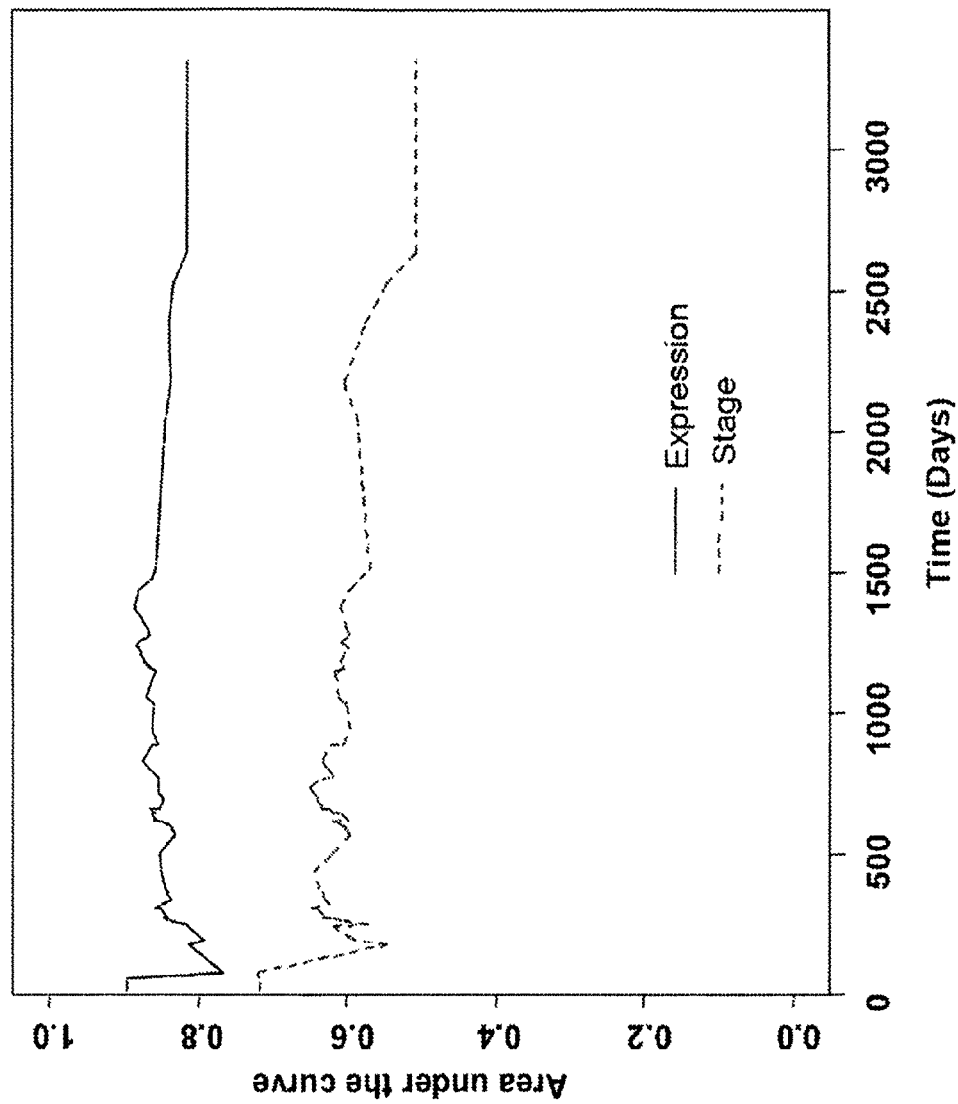

A comparison of FIGS. 4B and 4A clearly shows that the gene-expression signature has a much higher classification power than the staging method. The former had larger area between the two risk groups and smaller p value from the Mantel-Haenszel log rank test. FIG. 4C shows the time-dependent area under the receiver operating characteristic (ROC) curves based on the stage information or the estimated risk scores of the patients. The Cox model with gene expression data gave the better predictive performance with the AUCs (area under curve) close to 80%, whereas those with the stage information resulted in AUCs <60%.

Example 5

Confirmation of Gene Expression Signature in Predicting Survival

To confirm the prediction power of the 64-gene expression signature, the calculated risk score was compared to the know outcome of patients. Patients with a postoperative survival of at least 5 years and those who survived less than 2 years after surgical resection were selected for estimating the predictive power of Kaplan-Meier survival analysis using expression profiles. According to the risk scores estimated by the partial Cox regression approach, 77 out of the 88 patients were classified correctly (87% accuracy) (Table 4). Gene expression patterns were determined using hierarchical clustering of the 197 NSCLC samples against the 64 top survival-related genes (Lu et al. in press, PLoS Medicine). Short- and long-term survival NSCLC patients had quite distinct expression patterns among the 64 genes that were used for establishing a gene expression signature predictive of stage I NSCLC survival.

TABLE 4

Partial Cox regression classification using 64 survival-related genes

| Array | Death | Follow Up | Risk Score | Correct |
|---|---|---|---|---|
| 3196 | 0 | 1233 | −0.140 | |
| 3197 | 1 | 1299 | 0.020 | |
| 3198 | 0 | 856 | 0.155 | |
| 3199 | 0 | 2419 | −0.421 | Yes |
| 3200 | 1 | 336 | 0.033 | Yes |
| 3201 | 0 | 828 | −0.290 | |
| 3202 | 0 | 1812 | −0.069 | |
| 3203 | 0 | 555 | 0.148 | |
| 3204 | 1 | 1056 | 0.335 | |
| 3205 | 0 | 1166 | −0.132 | |
| 3206 | 0 | 1236 | 0.090 | |
| 3207 | 0 | 1314 | −0.187 | |
| 3208 | 0 | 1883 | −0.006 | Yes |
| 3209 | 0 | 338 | 0.014 | |
| 3210 | 1 | 658 | 0.169 | Yes |
| 3211 | 0 | 1842 | −0.121 | Yes |
| 3212 | 0 | 1648 | −0.091 | |
| 3213 | 0 | 1993 | −0.125 | Yes |
| 3214 | 1 | 307 | 0.214 | Yes |
| 3215 | 0 | 415 | 0.114 | |
| 3216 | 0 | 1748 | −0.021 | |
| 3217 | 0 | 2123 | −0.076 | Yes |
| 3218 | 0 | 1809 | 0.020 | |
| 3219 | 0 | 2471 | −0.124 | Yes |
| 3220 | 0 | 1648 | 0.016 | |
| 3221 | 0 | 2340 | −0.029 | Yes |
| 3222 | 0 | 2096 | −0.002 | Yes |
| 3223 | 0 | 987 | −0.163 | |
| 3224 | 0 | 2136 | −0.133 | Yes |
| 3225 | 0 | 1442 | −0.131 | |
| 3226 | 1 | 806 | 0.339 | |
| 3227 | 1 | 806 | 0.246 | |
| 3228 | 0 | 1624 | 0.038 | |
| 3229 | 1 | 54 | 0.144 | Yes |
| 3230 | 0 | 2276 | −0.150 | Yes |
| 3231 | 0 | 1709 | −0.032 | |
| AD111 | 0 | 2208 | −0.041 | Yes |
| AD114 | 0 | 2019 | −0.084 | Yes |
| AD118 | 1 | 1513 | −0.012 | |
| AD119 | 0 | 2336 | −0.157 | Yes |
| AD120 | 1 | 1186 | 0.125 | |
| AD131 | 0 | 2318 | 0.234 | No |
| AD136 | 0 | 958 | −0.041 | |
| AD158 | 1 | 1241 | 0.073 | |
| AD162 | 0 | 1272 | 0.037 | |
| AD167 | 0 | 1272 | −0.076 | |
| AD169 | 1 | 610 | 0.191 | Yes |
| AD170 | 0 | 2391 | −0.169 | Yes |
| AD178 | 1 | 885 | 0.059 | |
| AD179 | 1 | 741 | 0.086 | |
| AD183 | 0 | 1287 | −0.199 | |
| AD186 | 0 | 2574 | −0.135 | Yes |
| AD187 | 1 | 2632 | −0.019 | Yes |
| AD188 | 1 | 659 | −0.037 | No |
| AD203 | 0 | 3236 | −0.049 | Yes |
| AD207 | 1 | 2037 | −0.057 | Yes |
| AD210 | 0 | 1809 | −0.019 | |
| AD212 | 0 | 1800 | −0.179 | |
| AD224 | 0 | 1662 | −0.070 | |
| AD225 | 1 | 79 | 0.047 | Yes |
| AD226 | 0 | 1845 | −0.108 | Yes |
| AD228 | 1 | 1257 | 0.011 | |
| AD230 | 0 | 1729 | 0.042 | |
| AD236 | 1 | 433 | 0.219 | Yes |
| AD238 | 1 | 766 | 0.070 | |
| AD239 | 0 | 1784 | 0.004 | |
| AD240 | 0 | 1327 | −0.057 | |
| AD243 | 0 | 1528 | −0.064 | |
| AD247 | 0 | 2169 | −0.071 | Yes |
| AD249 | 1 | 946 | 0.190 | |
| AD250 | 0 | 2776 | 0.011 | No |
| AD252 | 1 | 503 | 0.153 | Yes |
| AD255 | 0 | 1366 | −0.013 | |
| AD258 | 1 | 375 | 0.127 | Yes |
| AD260 | 1 | 641 | 0.081 | Yes |
| AD261 | 0 | 1757 | −0.043 | |
| AD266 | 1 | 1278 | −0.029 | |
| AD267 | 0 | 1708 | −0.213 | |
| AD268 | 0 | 1528 | −0.049 | |
| AD269 | 1 | 1473 | −0.143 | |
| AD277 | 1 | 250 | 0.002 | Yes |
| AD283 | 1 | 1440 | −0.016 | |
| AD294 | 0 | 1235 | −0.087 | |
| AD295 | 0 | 1388 | 0.174 | |
| AD299 | 1 | 1156 | 0.134 | |
| AD301 | 1 | 238 | 0.196 | Yes |
| AD304 | 1 | 250 | 0.153 | Yes |
| AD308 | 0 | 2410 | 0.014 | No |
| AD309 | 1 | 1147 | −0.083 | |
| AD311 | 0 | 1540 | −0.190 | |
| AD313 | 1 | 772 | 0.064 | |
| AD317 | 1 | 3023 | −0.322 | Yes |
| AD318 | 0 | 2532 | −0.091 | Yes |
| AD320 | 0 | 2620 | 0.002 | No |
| AD327 | 0 | 2498 | −0.183 | Yes |
| AD331 | 0 | 1613 | 0.018 | |
| AD336 | 1 | 644 | 0.129 | Yes |
| AD346 | 0 | 528 | −0.037 | |
| AD347 | 0 | 15 | −0.193 | |
| AD353 | 0 | 418 | −0.169 | |
| AD356 | 0 | 1501 | −0.186 | |
| AD361 | 1 | 195 | 0.091 | Yes |
| AD362 | 1 | 2181 | −0.026 | Yes |
| AD363 | 1 | 320 | 0.052 | Yes |
| AD367 | 0 | 2321 | −0.172 | Yes |
| AD368 | 0 | 1909 | −0.020 | Yes |
| AD374 | 1 | 268 | 0.127 | Yes |
| AD375 | 1 | 714 | 0.148 | Yes |
| 30002 | 0 | 502 | −0.147 | |
| 30005 | 0 | 108 | −0.109 | |
| 30007 | 0 | 248 | 0.043 | |
| 30016 | 0 | 355 | 0.060 | |
| 40430 | 1 | 830 | 0.166 | |
| 41923 | 0 | 1834 | 0.036 | No |
| 41932 | 0 | 1601 | −0.053 | |
| 42081 | 0 | 1975 | −0.171 | Yes |
| 42613 | 1 | 648 | 0.023 | Yes |
| 42616 | 0 | 1964 | −0.076 | Yes |
| 44656 | 0 | 1766 | −0.027 | |
| 44661 | 1 | 273 | 0.105 | Yes |
| 44680 | 0 | 1647 | −0.066 | |
| 44693 | 1 | 693 | 0.055 | Yes |
| 48521 | 0 | 1855 | −0.310 | Yes |
| 48536 | 0 | 1855 | −0.296 | Yes |
| 48549 | 0 | 1617 | 0.053 | |
| 48556 | 0 | 2017 | −0.150 | Yes |
| 57774 | 1 | 1237 | 0.251 | |
| 76981 | 1 | 659 | 0.099 | Yes |
| 86011 | 1 | 620 | 0.245 | Yes |
| 86043 | 1 | 320 | 0.272 | Yes |
| AD10 | 1 | 2523 | 0.007 | No |
| AD2 | 0 | 2754 | 0.034 | No |
| AD3 | 0 | 2811 | −0.138 | Yes |
| AD5 | 0 | 3246 | −0.253 | Yes |
| AD6 | 1 | 1038 | −0.014 | |
| AD7 | 0 | 2043 | −0.255 | Yes |
| AD8 | 0 | 1026 | 0.110 | |
| L01 | 0 | 1410 | 0.018 | |
| L02 | 0 | 1173 | −0.142 | |
| L04 | 1 | 1374 | 0.081 | |
| L05 | 0 | 3318 | −0.082 | Yes |
| L06 | 0 | 2757 | 0.026 | No |
| L08 | 0 | 3237 | −0.144 | Yes |
| L09 | 0 | 2961 | −0.151 | Yes |
| L100 | 0 | 1314 | 0.225 | |
| L101 | 0 | 1200 | 0.021 | |
| L102 | 0 | 1200 | 0.276 | |
| L103 | 0 | 924 | 0.078 | |
| L104 | 0 | 732 | 0.014 | |
| L105 | 0 | 849 | −0.111 | |

TABLE 4-continued

Partial Cox regression classification using 64 survival-related genes

| Array | Death | Follow Up | Risk Score | Correct |
|---|---|---|---|---|
| L106 | 0 | 759 | −0.196 | |
| L107 | 0 | 390 | 0.200 | |
| L108 | 0 | 585 | 0.276 | |
| L11 | 1 | 1041 | 0.033 | |
| L111 | 0 | 45 | 0.052 | |
| L12 | 0 | 2556 | −0.028 | Yes |
| L13 | 1 | 2385 | −0.012 | Yes |
| L17 | 0 | 2511 | −0.084 | Yes |
| L18 | 0 | 1446 | −0.187 | |
| L20 | 1 | 597 | 0.143 | Yes |
| L22 | 0 | 375 | 0.220 | |
| L24 | 0 | 48 | 0.161 | |
| L25 | 0 | 435 | −0.097 | |
| L26 | 0 | 531 | 0.070 | |
| L27 | 0 | 633 | 0.039 | |
| L30 | 0 | 606 | 0.141 | |
| L31 | 0 | 756 | 0.075 | |
| L41 | 1 | 252 | 0.132 | Yes |
| L42 | 0 | 1902 | 0.058 | No |
| L43 | 0 | 2355 | −0.013 | Yes |
| L45 | 1 | 888 | −0.027 | |
| L45 | 0 | 2472 | −0.051 | Yes |
| L47 | 0 | 1815 | −0.090 | |
| L48 | 0 | 2234 | −0.036 | Yes |
| L49 | 0 | 2121 | −0.226 | Yes |
| L50 | 1 | 570 | −0.002 | No |
| L52 | 0 | 1962 | −0.007 | Yes |
| L56 | 0 | 1854 | −0.160 | Yes |
| L57 | 0 | 1644 | −0.044 | |
| L61 | 1 | 618 | 0.211 | Yes |
| L64 | 0 | 1443 | 0.029 | |
| L65 | 0 | 1587 | −0.136 | |
| L76 | 0 | 2631 | −0.229 | Yes |
| L78 | 0 | 1095 | 0.018 | |
| L79 | 1 | 261 | 0.166 | Yes |
| L80 | 1 | 303 | 0.194 | Yes |
| L81 | 0 | 1080 | 0.215 | |
| L82 | 0 | 1023 | −0.205 | |
| L83 | 0 | 918 | 0.059 | |
| L84 | 0 | 966 | −0.014 | |
| L85 | 0 | 804 | 0.100 | |
| L86 | 0 | 303 | −0.077 | |
| L87 | 0 | 312 | −0.063 | |
| L88 | 0 | 249 | 0.522 | |
| L90 | 1 | 174 | 0.581 | Yes |
| L97 | 0 | 147 | −0.209 | |
| L99 | 0 | 135 | 0.126 | |

0 = Alive
1 = Deceased

Example 6

Confirmation of Gene Signature Using Independent Datasets

The robustness of the 64-gene expression signature in predicting survival in lung cancer was further tested using oligonucleotide gene expression data obtained from two completely independent datasets. Dataset 6 was from Gerald et al. (unpublished data) and included 63 stage I lung adenocarcinomas, of which 9 patients survived for at least 5 years and 5 survived less than 2 years after surgery. Dataset 7 was from Bild et al. (2006, Nature 439:353-357) and included 64 stage I lung adenocarcinomas (GEO accession number GSE3141), of which 8 patients survived for at least 5 years and 12 survived less that 2 years after surgery.

Figure 5A:
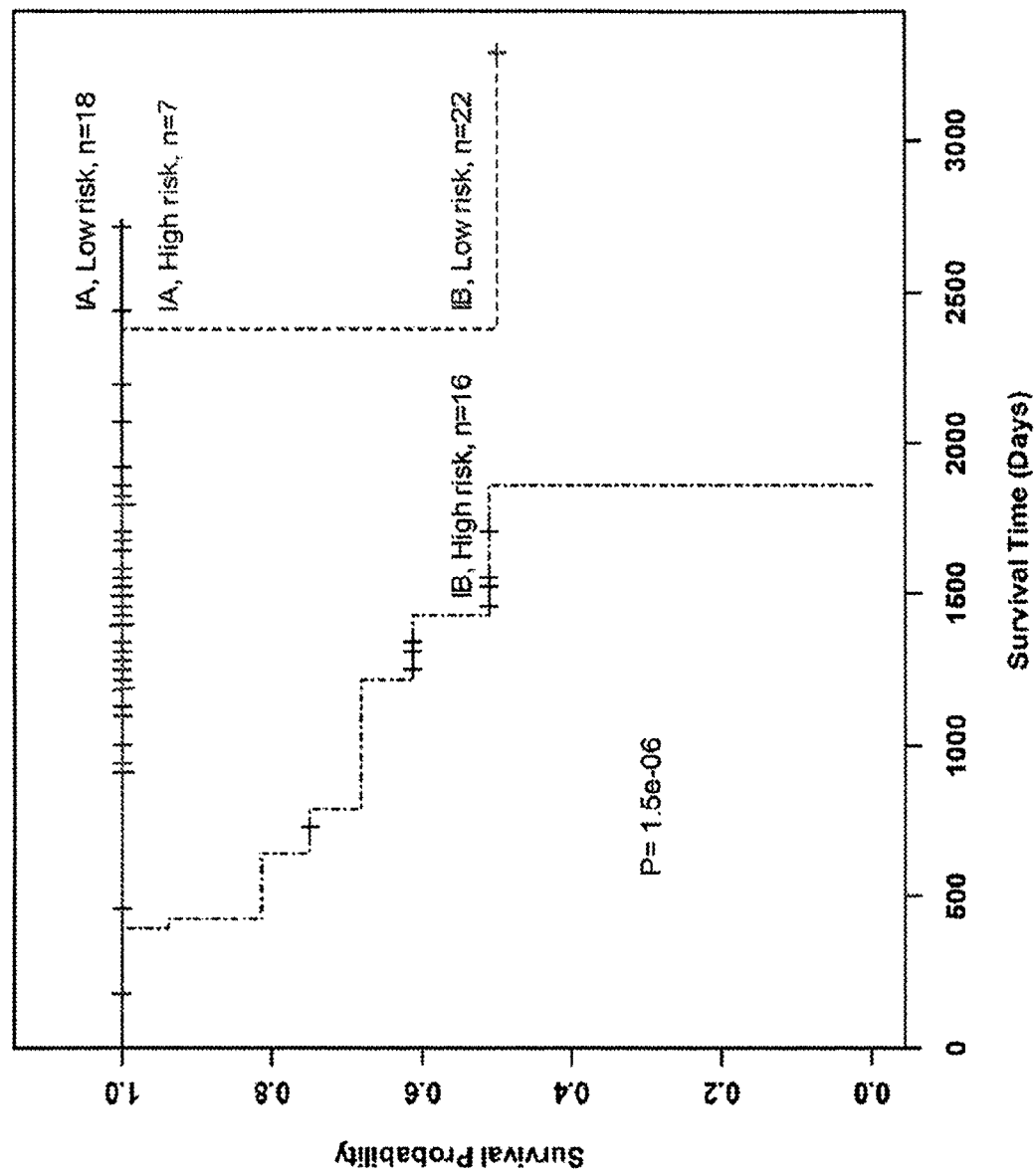
FIG. 5 shows graphs depicting the predictive accuracy of the 64-gene expression signature. Panel (A) presents Kaplan-Meier survival curves for dataset 6 (Gerald et al., unpublished) and panel (B) presents Kaplan-Meier survival curves for dataset 7 (Bild et al., 2006, Nature 439:353-357).
Figure 5B:
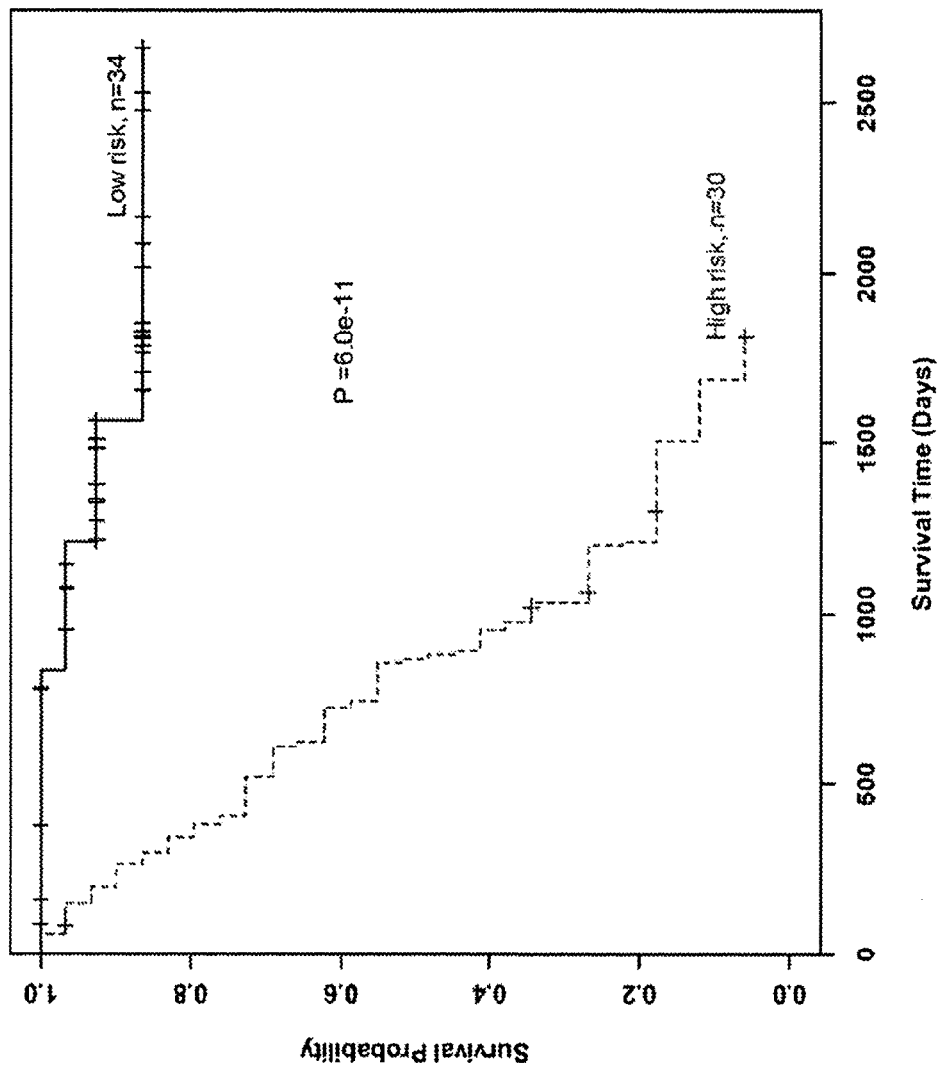

The risk assignment of the samples in these two datasets was examined using the risk scores based on the 64-gene signature. The scores in dataset 6 were estimated using 2 principal components and the scores in dataset 7 were estimated using 8 principal components. It was found that the high and low risk groups differed significantly in survivals in datasets 6 and 7. Using the 64-gene signature, 1 out of 14 the individuals was classified incorrectly (93% accuracy) in dataset 6 (P=1.5e-6; FIG. 5A). All of the 20 patients that survived for at least 5 years or survived less than 2 years in dataset 7 were correctly classified using the 64-gene signature (P=6.0e-11; FIG. 5B). The risk assignment of the samples in these two datasets was also examined using the risk scores based on the 50-gene signature reported by Beer et al. (2001). This gene signature provided less accurate classification; dataset 6 (P=9.15e-05) and dataset 7 (P=1.2e-10). In particular, three patients in dataset 6 who survived for more than 5 years and one patient in dataset 7 who survived for more than 2476 days were classified into the low risk group according the risk scores calculated by the 64-gene gene signature, but all of them were classified into the high risk group using the 50-gene gene signature.

What is claimed is:

1. A plurality of biomarkers for predicting survival of a subject with a lung cancer, the plurality of biomarkers comprising isolated APC, isolated ARHGEF1, isolated BCL2, isolated CASP10, isolated CASF8, isolated CCR2, isolated CDH8, isolated DTNA, isolated ENPP2, isolated FUCA1, isolated GNAT2, isolated GOLGA1, isolated IL8RB, isolated ITSN1, isolated MAP4K1, isolated MEF2C, isolated MLLT10, isolated NR1H4, isolated NTRK3, isolated PBP, isolated PICC, isolated PIK3R1, isolated PKNOX1, isolated PPDX, isolated PRKACA, isolated RAB28, isolated RAE1, isolated SNX1, isolated SON, isolated TMSB4X, isolated TRA2A, isolated ZNFN1A1, isolated ABCC1, isolated ADAM17, isolated ARL4A, isolated BIK, isolated BLM, isolated CHERP, isolated CRABP1, isolated DSP, isolated FBN2, isolated GLI2, isolated HNRPD, isolated INHA, isolated IRS1, isolated LARS2, isolated LY6D, isolated NID, isolated NOTCH3, isolated PCDHGA12, isolated PFN2, isolated PLEC1, isolated PSEN1, isolated PYGL, isolated SLC2A1, isolated SLC7A1, isolated SMC1L1, isolated SMARCA3, isolated STC1, isolated UPK2, isolated VGLL1, isolated ZNF154, isolated ZNF410, and isolated ZWINTAS.

* * * * *

UNITED STATES PATENT AND TRADEMARK OFFICE
CERTIFICATE OF CORRECTION

PATENT NO.        : 8,202,968 B2                              Page 1 of 1
APPLICATION NO.   : 12/445596
DATED             : June 19, 2012
INVENTOR(S)       : Ming You et al.

It is certified that error appears in the above-identified patent and that said Letters Patent is hereby corrected as shown below:

Col. 31, line 28 (Claim 1, line 4): "CASF8" should read --CASP8--

Col. 31, line 33 (Claim 1, line 9): "PICC" should read --PIGC--

Col. 31, line 34 (Claim 1, line 10): "PPDX" should read --PPOX--

Signed and Sealed this
Eleventh Day of September, 2012

David J. Kappos
*Director of the United States Patent and Trademark Office*

SEQUENCE LISTING

<160> NUMBER OF SEQ ID NOS: 20

<210> SEQ ID NO 1
<211> LENGTH: 21
<212> TYPE: DNA
<213> ORGANISM: Homo sapiens

<400> SEQUENCE: 1
caagagatgg ccagggctgc t        21

<210> SEQ ID NO 2
<211> LENGTH: 21
<212> TYPE: DNA
<213> ORGANISM: Homo sapiens

<400> SEQUENCE: 2
tccttctgca tcctgtcggc a          21

<210> SEQ ID NO 3
<211> LENGTH: 16
<212> TYPE: DNA
<213> ORGANISM: Homo sapiens

<400> SEQUENCE: 3
gccacgggcg aaaagc          16

<210> SEQ ID NO 4
<211> LENGTH: 19
<212> TYPE: DNA
<213> ORGANISM: Homo sapiens

<400> SEQUENCE: 4
cacgtgggag gtgccataa          19

<210> SEQ ID NO 5
<211> LENGTH: 21
<212> TYPE: DNA
<213> ORGANISM: Homo sapiens

<400> SEQUENCE: 5
catgtgtgtg gagagcgtca a          21

<210> SEQ ID NO 6
<211> LENGTH: 21
<212> TYPE: DNA
<213> ORGANISM: Homo sapiens

<400> SEQUENCE: 6
gccggttcag gtactcagtc a          21

<210> SEQ ID NO 7
<211> LENGTH: 17
<212> TYPE: DNA
<213> ORGANISM: Homo sapiens

<400> SEQUENCE: 7
gtagcggctg cgtccaa          17

<210> SEQ ID NO 8
<211> LENGTH: 20
<212> TYPE: DNA
<213> ORGANISM: Homo sapiens

<400> SEQUENCE: 8
ccgtggtgga tgtcttgatg          20

<210> SEQ ID NO 9
<211> LENGTH: 22
<212> TYPE: DNA
<213> ORGANISM: Homo sapiens

<400> SEQUENCE: 9
tgcttctggc agtggtcctt ct          22

<210> SEQ ID NO 10
<211> LENGTH: 22
<212> TYPE: DNA
<213> ORGANISM: Homo sapiens

```
<400> SEQUENCE: 10
tcctccttgg tgcctctctt gt                                        22

<210> SEQ ID NO 11
<211> LENGTH: 17
<212> TYPE: DNA
<213> ORGANISM: Homo sapiens

<400> SEQUENCE: 11
cgagtggcgg ctcaaaa                                              17

<210> SEQ ID NO 12
<211> LENGTH: 18
<212> TYPE: DNA
<213> ORGANISM: Homo sapiens

<400> SEQUENCE: 12
ccgcagccga cctgtaga                                             18

<210> SEQ ID NO 13
<211> LENGTH: 26
<212> TYPE: DNA
<213> ORGANISM: Homo sapiens

<400> SEQUENCE: 13
catgcaggcc taagtatatg ttgtgt                                    26

<210> SEQ ID NO 14
<211> LENGTH: 18
<212> TYPE: DNA
<213> ORGANISM: Homo sapiens

<400> SEQUENCE: 14
tgcacccaaa gcgagtga                                             18

<210> SEQ ID NO 15
<211> LENGTH: 23
<212> TYPE: DNA
<213> ORGANISM: Homo sapiens

<400> SEQUENCE: 15
cagaaagcac cacccatatg att                                       23

<210> SEQ ID NO 16
<211> LENGTH: 19
<212> TYPE: DNA
<213> ORGANISM: Homo sapiens

<400> SEQUENCE: 16
gaggccagca tggtaagca                                            19

<210> SEQ ID NO 17
<211> LENGTH: 18
<212> TYPE: DNA
<213> ORGANISM: Homo sapiens

<400> SEQUENCE: 17
atggtgcccg tcaatgct                                             18

<210> SEQ ID NO 18
<211> LENGTH: 23
<212> TYPE: DNA
<213> ORGANISM: Homo sapiens
```

```
<400> SEQUENCE: 18
cgattgtctt tgctcttcat gtg                                            23

<210> SEQ ID NO 19
<211> LENGTH: 22
<212> TYPE: DNA
<213> ORGANISM: Homo sapiens

<400> SEQUENCE: 19
cctctcagtg gccatctttt ct                                             22

<210> SEQ ID NO 20
<211> LENGTH: 17
<212> TYPE: DNA
<213> ORGANISM: Homo sapiens

<400> SEQUENCE: 20
ccggccaaag cggttaa                                                   17
```